(12) United States Patent
Hegmann et al.

(10) Patent No.: US 10,709,815 B2
(45) Date of Patent: Jul. 14, 2020

(54) BIODEGRADABLE, BIOCOMPATIBLE 3D LIQUID CRYSTAL ELASTOMERIC FOAM SCAFFOLDS HAVING TAILOR-MADE ANIMAL (HUMAN) PORE CELL SIZES VIA A SALT LEACHING METHOD ARE CAPABLE OF GROWING TISSUE THEREIN FOR THERAPEUTIC RECONSTRUCTION OF DAMAGED AND/OR DISEASED TISSUE OR ORGANS

(71) Applicant: KENT STATE UNIVERSITY, Kent, OH (US)

(72) Inventors: Elda Hegmann, Kent, OH (US); Marianne E. Prévôt, Kent, OH (US); Torsten Hegmann, Kent, OH (US)

(73) Assignee: Kent State University, Kent, OH (US)

( * ) Notice: Subject to any disclaimer, the term of this patent is extended or adjusted under 35 U.S.C. 154(b) by 137 days.

(21) Appl. No.: 15/800,446

(22) Filed: Nov. 1, 2017

(65) Prior Publication Data

US 2019/0111185 A1 Apr. 18, 2019

Related U.S. Application Data

(60) Provisional application No. 62/572,902, filed on Oct. 16, 2017.

(51) Int. Cl.
| | |
|---|---|
| *A61L 27/56* | (2006.01) |
| *C08G 18/28* | (2006.01) |
| *A61L 27/58* | (2006.01) |
| *A61K 9/70* | (2006.01) |
| *A61L 27/16* | (2006.01) |

(Continued)

(52) U.S. Cl.
CPC ............ *A61L 27/56* (2013.01); *A61K 9/7023* (2013.01); *A61L 27/14* (2013.01); *A61L 27/16* (2013.01); *A61L 27/38* (2013.01); *A61L 27/383* (2013.01); *A61L 27/3804* (2013.01); *A61L 27/3808* (2013.01); *A61L 27/3821* (2013.01); *A61L 27/3826* (2013.01); *A61L 27/3834* (2013.01); *A61L 27/50* (2013.01); *A61L 27/58* (2013.01); *A61L 27/60* (2013.01); *C08G 18/283* (2013.01); *C08G 18/4263* (2013.01); *C08G 18/4269* (2013.01); *C08G 18/4277* (2013.01); *C08G 18/48* (2013.01); *C08J 9/26* (2013.01); *A61L 2430/02* (2013.01); *A61L 2430/32* (2013.01);

(Continued)

(58) Field of Classification Search
CPC ....... A61K 9/7023; A61L 27/14; A61L 27/16; A61L 27/38; A61L 27/3804; A61L 27/3808; A61L 27/3821; A61L 27/3826; A61L 27/383; A61L 27/3834; A61L 27/50; A61L 27/56; A61L 27/58; A61L 27/60; A61L 2430/02; A61L 2430/32; A61L 2430/34; C08G 18/283; C08G 18/4263; C08G 18/4269; C08G 18/4277; C08G 18/48; C08J 9/26; C08J 2201/0422; C08J 2201/0444

See application file for complete search history.

(56) References Cited

U.S. PATENT DOCUMENTS

| | | | |
|---|---|---|---|
| 8,067,031 B2* | 11/2011 | Daniloff ............... | A61K 9/1075 424/484 |
| 9,815,935 B2* | 11/2017 | Hegmann .............. | C08G 63/08 |

(Continued)

FOREIGN PATENT DOCUMENTS

| | | |
|---|---|---|
| WO | WO-2014172261 A1 * | 10/2014 |
| WO | WO-2015095768 A1 * | 6/2015 |

OTHER PUBLICATIONS

Kular, J. et al., The Extracellular Matrix: Structure, Composition, Age-Related Differences, Tools for Analysis and Applications for Tissue Engineering, Journal of Tissue Engineering, 2014, pp. 1-17, vol. 5.

(Continued)

*Primary Examiner* — John M Cooney
(74) *Attorney, Agent, or Firm* — Hudak, Shunk & Farine Co. LPA

(57) ABSTRACT

Star block copolymers having 3 to 8 arms are formed as a 3D foam scaffold having tailor-made pore sizes that mimic an actual cell size of a specific animal and/or human tissue and/or organs. The pore sizes are made within the elastomeric foams via a salt leaching process wherein a salt of a specific particle size is blended within the star block copolymers and crosslinked as by polyisocyanate compounds. Water or other suitable solvent are utilized to dissolve and leach out the salt leaving an open pore system. Animal and/or human cells are then injected into the 3D elastomeric foam scaffold that contains pendant liquid crystals on the star block copolymer whereby with the aid of nutrients, cells are formed within the pore system that are viable for at least three months. The size of the pore is predetermined to produce a desired cultured cell having a desired size. The tissue and/or cells within the elastomeric scaffold can be applied to animal and/or human tissue and/or organs whereupon they grow and reconstruct the damaged, injured, diseased, etc., area and result in a healthy, repaired, and viable tissue or organ. The elastomeric liquid crystal containing foam scaffold will degrade naturally and/or also be consumed by the growing cells so that it no longer exists. In other words, a specific type of animal or human cell can be culturally produced having a predetermined average cell diameter that is substantially or essentially the same diameter of a natural cell.

20 Claims, 40 Drawing Sheets

(51) Int. Cl.
| | |
|---|---|
| *A61L 27/38* | (2006.01) |
| *A61L 27/50* | (2006.01) |
| *A61L 27/14* | (2006.01) |
| *A61L 27/60* | (2006.01) |
| *C08J 9/26* | (2006.01) |
| *C08G 18/48* | (2006.01) |
| *C08G 18/42* | (2006.01) |

(52) U.S. Cl.
CPC ... *A61L 2430/34* (2013.01); *C08J 2201/0422* (2013.01); *C08J 2201/0444* (2013.01)

(56) References Cited

U.S. PATENT DOCUMENTS

| | | | | |
|---|---|---|---|---|
| 2003/0235602 | A1* | 12/2003 | Schwarz | A61L 27/34 424/424 |
| 2016/0046761 | A1* | 2/2016 | Hegmann | C08G 63/08 521/182 |
| 2016/0339145 | A1* | 11/2016 | Hegmann | A61L 27/18 |

OTHER PUBLICATIONS

Langer, R. et al., Designing Materials for Biology and Medicine, Nature Publishing Group, 2004, pp. 487-492, vol. 428.

Lutolf, M. et al., Synthetic Biomaterials as Instructive Extracellular Microenvironments for Morphogenesis in Tissue Engineering, Nature Biotechnology, 2005, pp. 47-55, vol. 23, No. 1.

Place, E. et al., Complexity in Biomaterials for Tissue Engineering, Nature Materials, 2009, pp. 457-470, vol. 8, Macmillan Publishers Ltd.

Kyburz, K. et al., Synthetic Mimics of the Extracellular Matrix: How Simple is Complex Enough?, Annals of Biomedical Engineering, 2015, pp. 489-500, vol. 43, No. 3.

Rnjak-Kovacina, J. et al., Lyophilized Silk Sponges: A Versatile Biomaterial Platform for Soft Tissue Engineering, ACS Biomaterials Science & Engineering, 2015, pp. 260-270, vol. 1.

Lendlein, A. et al., Biodegradable, Elastic Shape-Memory Polymers for Potential Biomedical Applications, Science, 2002, pp. 1673-1676, vol. 296.

Coombes, A.G.A. et al., Precipitation Casting of Polycaprolactone for Applications in Tissue Engineering and Drug Delivery, Biomaterials, 2004, pp. 315-325, vol. 25.

Dankers, P. et al., A Modular and Supramolecular Approach to Bioactive Scaffolds for Tissue Engineering, Nature Materials, 2005, pp. 568-574, vol. 4.

Atala, A. et al., Tissue-Engineered Autologous Bladders for Patients Needing Cystoplasty, Lancet, 2006, pp. 1241-1246, vol. 367.

Rapoport, N., Physical Stimuli-Responsive Polymeric Micelles for Anti-Cancer Drug Delivery, Prog. Polymer Science, 2007, pp. 962-990, vol. 32.

Williams, D., On the Mechanisms of Biocompatibility, Biomaterials, 2008, pp. 2941-2953, vol. 29.

Zimmerman, W., Polymers Flex Their Muscles, Nature Materials, 2008, pp. 932-933, vol. 7.

Lou, C. et al., Manufacturing and Properties of PLA Absorbable Surgical Suture, Textile Research Journal, 2008, pp. 958-965, vol. 78.

Byrne, C. et al., Catalytic Synthesis of β3-Amino Acid Derivatives from α-Amino Acids, Angewandte Chem. Int. Ed., 2008, pp. 3979-3983, vol. 47.

Yuksel, E. et al., Challenges in Soft Tissue Engineering, Seminars in Plastic Surgery, 2005, pp. 261-270, vol. 19, No. 3.

Pelham, R. et al., Cell Locomotion and Focal Adhesions are Regulated by Substrate Flexibility, Proc. Natl. Acad. Sci. USA, 1997, pp. 13661-13665, vol. 94.

Engler, A. et al., Matrix Elasticity Directs Stem Cell Lineage Specification, Cell, 2006, pp. 677-689, vol. 126.

Li, W. et al., Engineering Controllable Anisotropy in Electrospun Biodegradable Nanofibrous Scaffolds for Musculoskeletal Tissue Engineering, Journal of Biomechanics, 2007, pp. 1686-1693, vol. 40.

Millon, L., et al., Anisotropic Polyvinyl Alcohol Hydrogel for Cardiovascular Applications, Journal of Biomedical Materials Research Part B: Applied Biomaterials, 2006, pp. 305-311, vol. 79.

Sun, B. et al., Electrospun Anisotropic Architectures and Porous Structures for Tissue Engineering, Journal of Materials Chemistry B, 2015, pp. 5389-5410, vol. 3.

Engelmayr, G. et al., Accordion-Like Honeycombs for Tissue Engineering of Cardiac Anisotropy, Nature Materials, 2008, pp. 1003-1010, vol. 7.

Cukierman, E. et al., Taking Cell-Matrix Adhesions to the Third Dimension, Science, 2001, pp. 1708-1712, vol. 294.

Stevens, M. et al., Exploring and Engineering the Cell Surface Interface, Science, 2005, pp. 1135-1138, vol. 310.

Hollister, S., Porous Scaffold Design for Tissue Engineering, Nature Materials, 2005, pp. 518-524, vol. 4.

Orr, A. et al., Mechanisms of Mechanotransduction, Developmental Cell, 2006, pp. 11-20, vol. 10.

Moutos, F. et al., A Biomimetic Three-Dimensional Woven Composite Scaffold for Functional Tissue Engineering of Cartilage, Nature Materials, 2007, pp. 162-167, vol. 6.

Lowe, A. et al., Liquid Crystalline Materials for Biological Applications, Chem. Mater., 2012, pp. 746-758, vol. 24.

Brand, H. et al., Physical Properties of Liquid Crystalline Elastomers, Handbook of Liquid Crystals, 1998, pp. 277-300, vol. 3.

De Gennes, P. et al., Artificial Muscles Based on Nematic Gels, Macromol. Symp., 1997, pp. 39-49, vol. 113.

Finkelmann, H. et al., Tunable Mirrorless Lasing in Cholesteric Liquid Crystalline Elastomers, Advanced Matrials, 2001, pp. 1069-1072, vol. 13, No. 14.

Camacho-Lopez, M. et al., Fast Liquid-Crystal Elastomer Swims into the Dark, Nature Materials, 2004, pp. 307-310, vol. 3.

Yu, Y. et al., Soft Actuators Based on Liquid-Crystalline Elastomers, Angew. Chem. Int. Ed., 2006, pp. 5416-5418, vol. 45.

Van Oosten, C. et al., Printed Artificial Cilia from Liquid-Crystal Network Actuators Modularly Driven by Light, Nature Materials, 2009, pp. 677-682, vol. 8.

Lockwood, N. et al., Thermotropic Liquid Crystals as Substrates for Imaging the Reorganization of Matrigel by Human Embryonic Stem Cells, Advanced Functional Materials, 2006, pp. 618-624, vol. 16.

Sharma, A. et al., Biocompatible, Biodegradable and Porous Liquid Crystal Elastomer Scaffolds for Spatial Cell Cultures, Macromolecular Bioscience, 2015, pp. 200-214, vol. 15.

Gao, Y. et al., Biocompatible 3D Liquid Crystal Elastomer Cell Scaffolds and Foams with Primary and Secondary Porous Architecture, ACS Macro Letters, 2016, pp. 4-9, vol. 5.

Bera, T. et al., Liquid Crystal Elastomer Microspheres as Three-Dimensional Cell Scaffolds Supporting the Attachment and Proliferation of Myoblasts, ACS Applied Materials & Interfaces, 2015, pp. 14528-14535, vol. 7.

Bera, T. et al., Role of Surfactant during Microemulsion Photopolymerization for the Creation of Three-Dimensional Liquid Crystal Elastomer Microsphere Spatial Cell Scaffolds, Frontiers in Materials, 2016, pp. 1-8, vol. 3, Article 31.

McKee, C. et al., Indentation Versus Tensile Measurements of Young's Modulus for Soft Biological Tissues, Tissue Engineering: Part B, 2011, pp. 155-164, vol. 17, No. 3.

Dahl, J. et al., Coordinate Regulation of Unsaturated Phospholipid, RNA, and Protein Synthesis in Mycoplasma Capricolum by Cholesterol, Proceedings of the National Academy of Sciences of the USA, 1983, pp. 692-696, vol. 80, No. 3.

Mauch, D. et al., CNS Synaptogenesis Promoted by Glia-Derived Cholesterol, Science, 2001, pp. 1354-1357, vol. 294.

Hwang, J. et al., Self-Assembling Biomaterials: Liquid Crystal Phases of Cholesteryl Oligo(L-Lactic Acid) and Their Interactions with Cells, Proceedings of the National Academy of Sciences of the USA, 2002, pp. 9662-9667, vol. 99, No. 15.

Nagahama, K. et al., Exhibition of Soft and Tenacious Characteristics Based on Liquid Crystal Formation by Introduction of Cho-

(56) References Cited

OTHER PUBLICATIONS lesterol Groups of Biodegradable Lactide Copolymer, Biomacromolecules, 2007, pp. 3938-3943, vol. 8.
Hexemer, A. et al., A SAXS/WAXS/GISAXS Beamline with Multilayer Monochromator, Journal of Physics: Conference Series 247, 2010, 012007, pp. 1-11.
Schneider, C. et al., NIH Image to ImageJ: 25 Years of Image Analysis, Nature Methods, 2012, pp. 671-675, vol. 9, No. 7.
Younes, H. et al., Synthesis, Characterization and in Vitro Degradation of a Biodegradable Elastomer, Biomaterials, 2004, pp. 5261-5269, vol. 25.
Binder, W. et al., 'Click' Chemistry in Polymer and Matrial Science: An Update, Macromolecular Rapid Communications, 2008, pp. 952-981, vol. 29.
Ratner, B. et al., Biomaterials: Where We Have Been and Where We Are Going, Annu. Rev. Biomed. Eng., 2004, pp. 41-75, vol. 6.
Armentano, I. et al., Biodegradable Polymer Matrix Nanocomposites for Tissue Engineering: A Review, Polymer Degradation and Stability, 2010, pp. 2126-2146, vol. 95.
Sakai, T., Experimental Verification of Homogeneity in Polymer Gels, Polymer Journal, 2014, pp. 517-523, vol. 46.
Nair, L. et al., Biodegradable Polymers as Biomaterials, Prog. Polymer Science, 2007, pp. 762-798, vol. 32.

\* cited by examiner

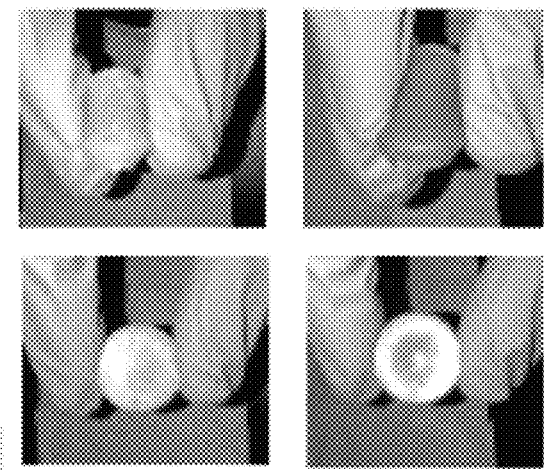
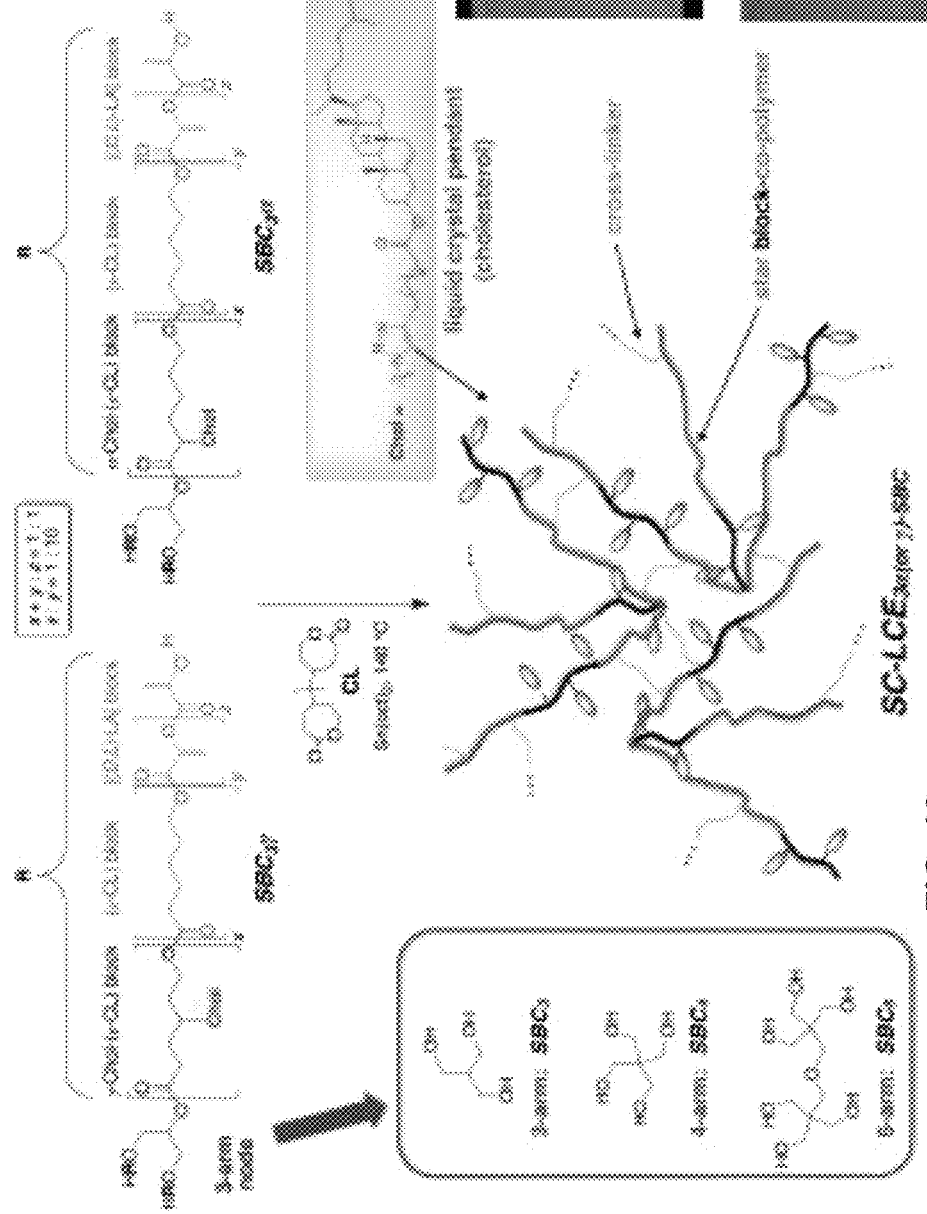
FIG. 13

Tissue engineering

Consists in the formation of functional substitutes for the therapeutic reconstruction of damaged or diseased tissues by the careful and controlled stimulation of molecular and mechanical signals Involves the design and use of a support that maintains tissue contour, particularly in the form of a 3D scaffold, implanted at the defective site, satisfying certain specific requirements:
- Elasticity
- Enhance attachment and viability (i.e. expansion)
- Anisotropy
- Responsiveness
- Geometry
- 3-Dimensionality
- Porosity

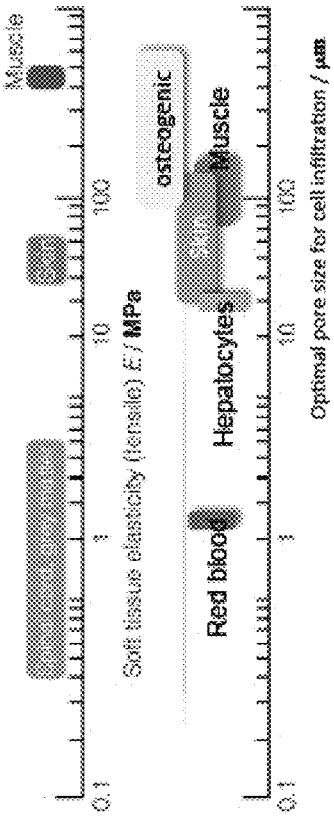

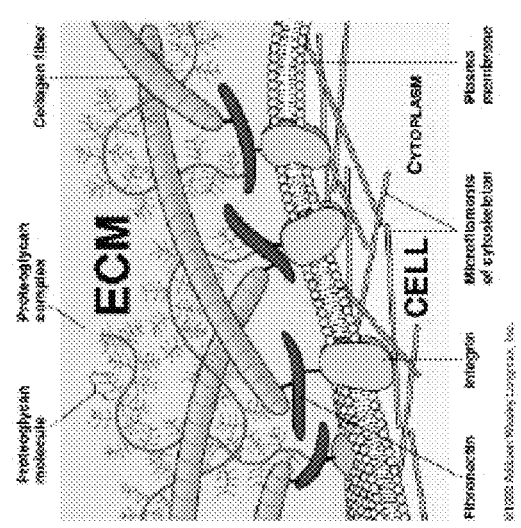

FIG. 15

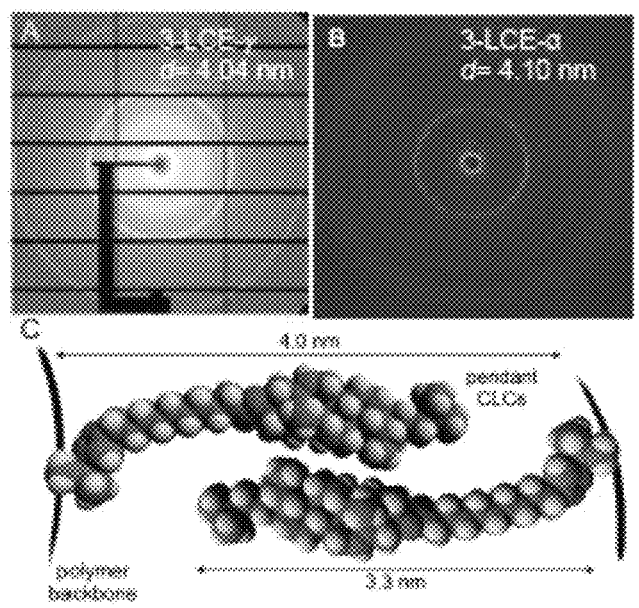
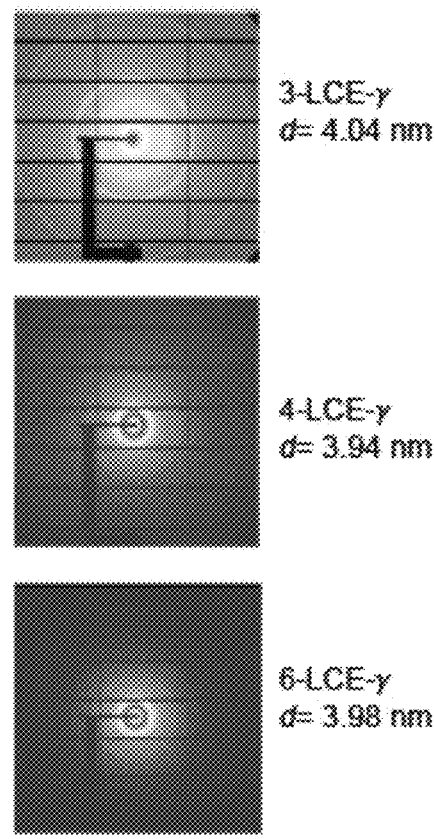
FIG. 17

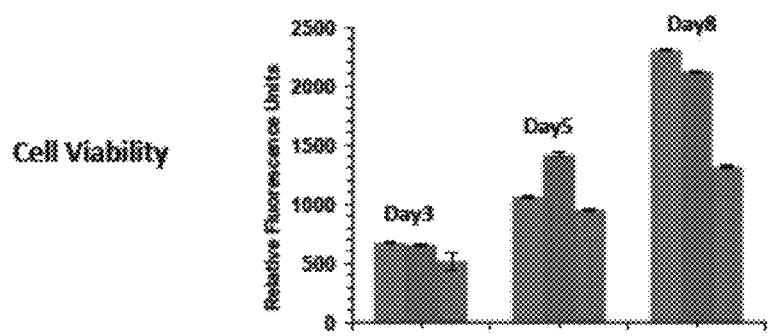
FIG. 19

Mechanical Properties of Tissues

TABLE 4. COMPARISON OF INDENTATION AND TENSILE MEASUREMENTS OF YOUNG'S MODULUS

*Indentation versus tensile*

| Tissue | Indentation (kPa) | Tensile (MPa) |
|---|---|---|
| Skin | ~85 | ~30 |
| L&K | ~190 | ~10 |
| Spinal cord & gray matter | ~3 | ~2 |
| Muscle | ~7 | ~480 |
| Tendon | No values | ~560 |
| Breast tissue | ~8 | No values |
| A&V | ~125 | ~2 |
| Sclera | No values | ~2.7 |
| Cornea | ~29 | ~3.0 |

The values are the averages without the suspected outliers. Of the tabled citations on tissue mechanics, eight reports did not clearly state the tissue hydration condition, and the rest were measured in "wet" or "hydrated" (such as skin) conditions. Of those eight, we considered only one as an indentation outlier.[139] The results in this table are therefore not changed by consideration of this variable.

"The scientific objective of a given research proposal therefore dictates which method is most appropriate."

FIG. 20

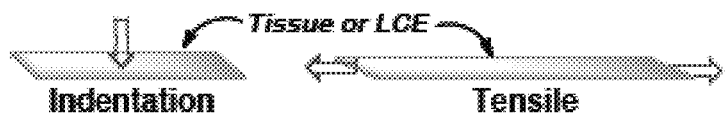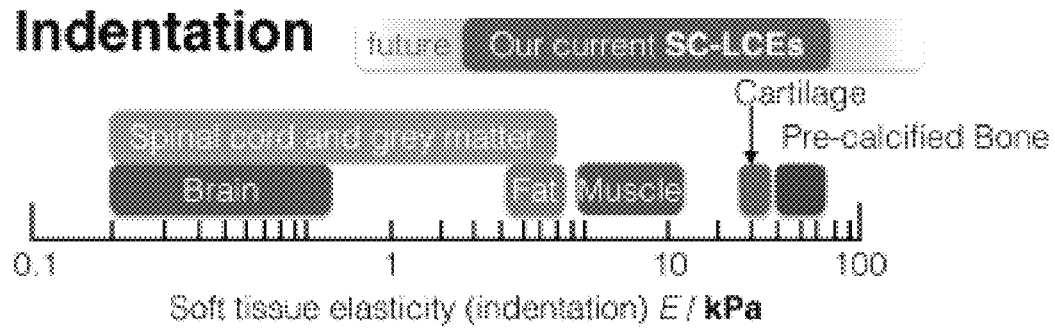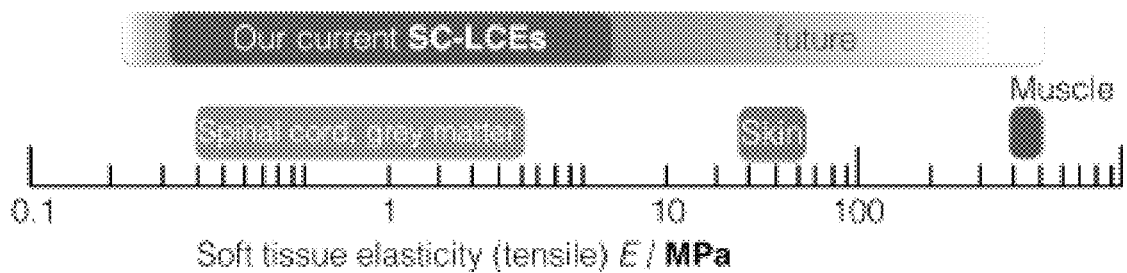
FIG. 21

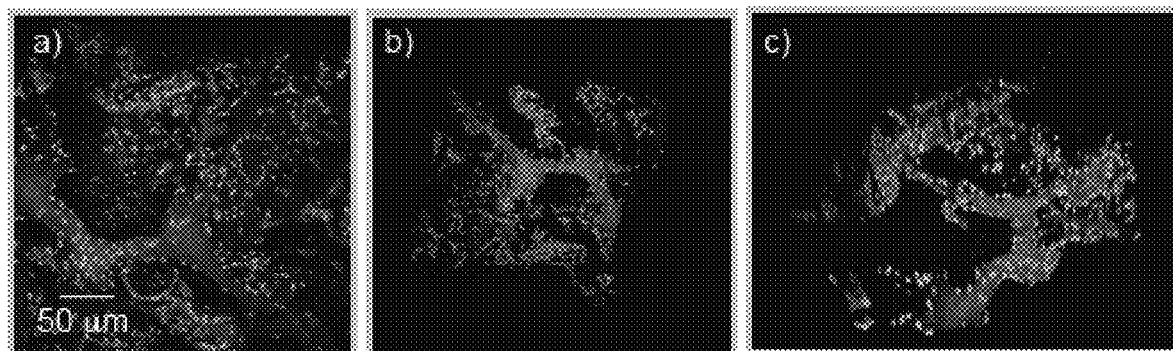
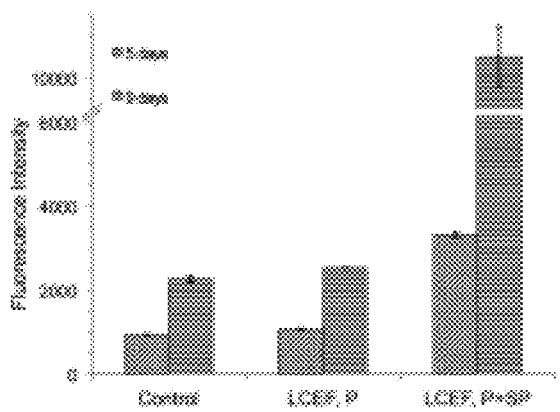
FIG. 26

(A) 2D images stacked on Z direction.
(B-D) 3D views from different angle.
Scale bar unit: μm

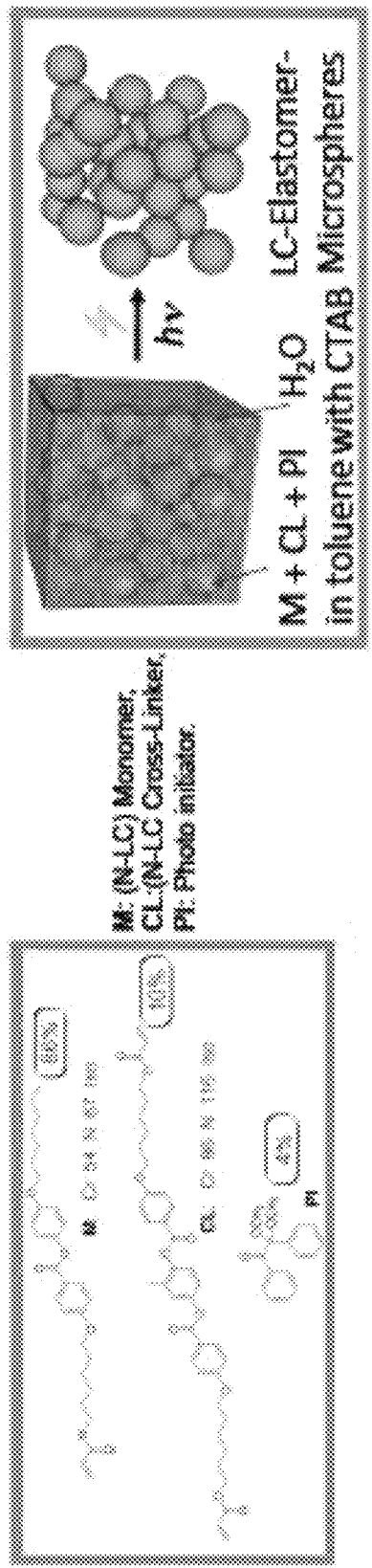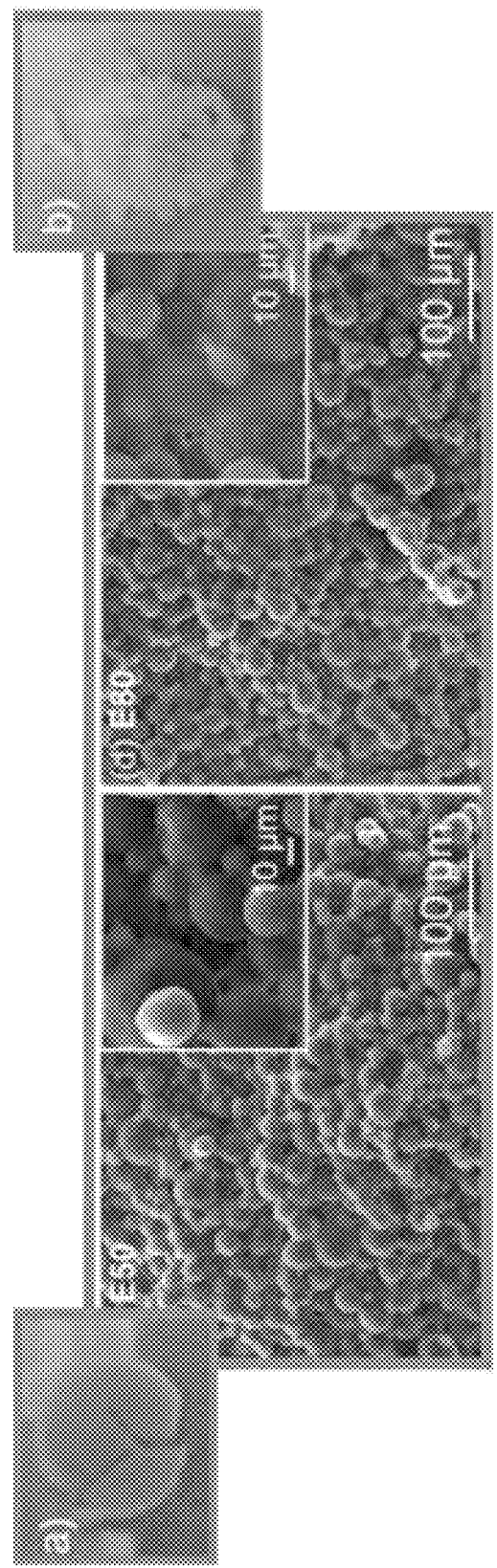
Inverted Porosity – Globular morphology of Nematic LCE
SEM images of LC-Elastomer-Microspheres. En: n = ratio% of H₂O in toluene
FIG. 29

Scanning electron micrographs, cells (false colored green) can be seen as extending fibers directly attaching to the matrix for expansion and proliferation

Conclusions

- Our LCEs are biocompatible and biodegradable
- Slight modification in central node results in different mechanical and cellular response
- Biomechanical studies of elastomers with growing viable cells are ongoing.
- Created LCE scaffolds for 3D cell culture and tissue regeneration.
- First example of biocompatible N LCEs that mimic artificial muscle as scaffolds for muscle cells
- *3D spatial orientation and alignment works with the most challenging entities, living cells. Semiconductor or metal nano- or microstructures (metamaterials) should be easier*

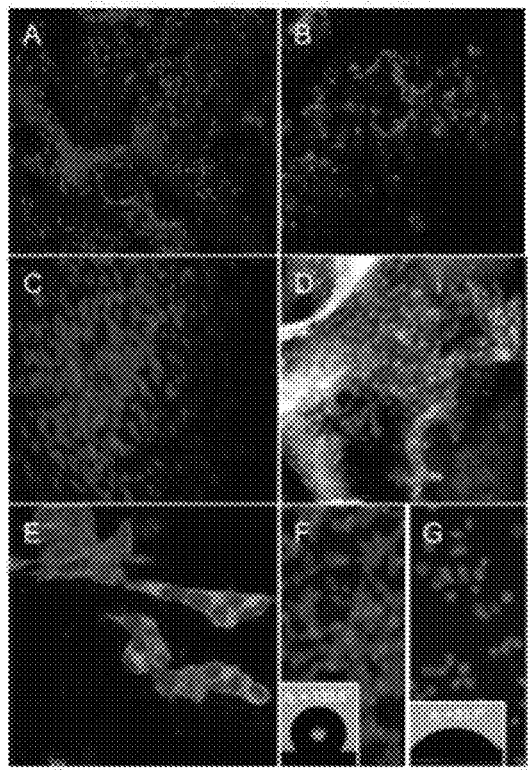

FIG. 40

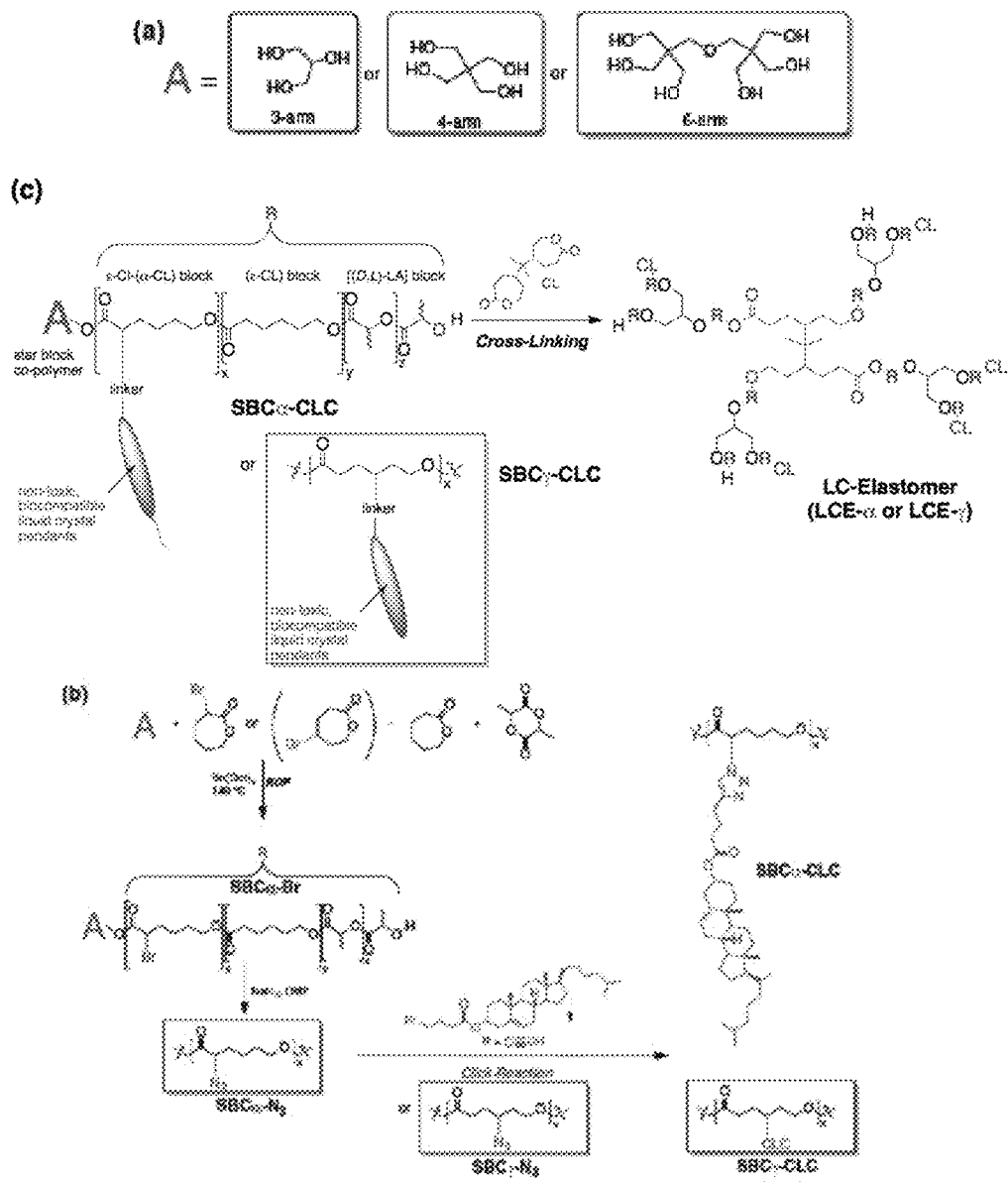
FIG. 41 - Scheme 1

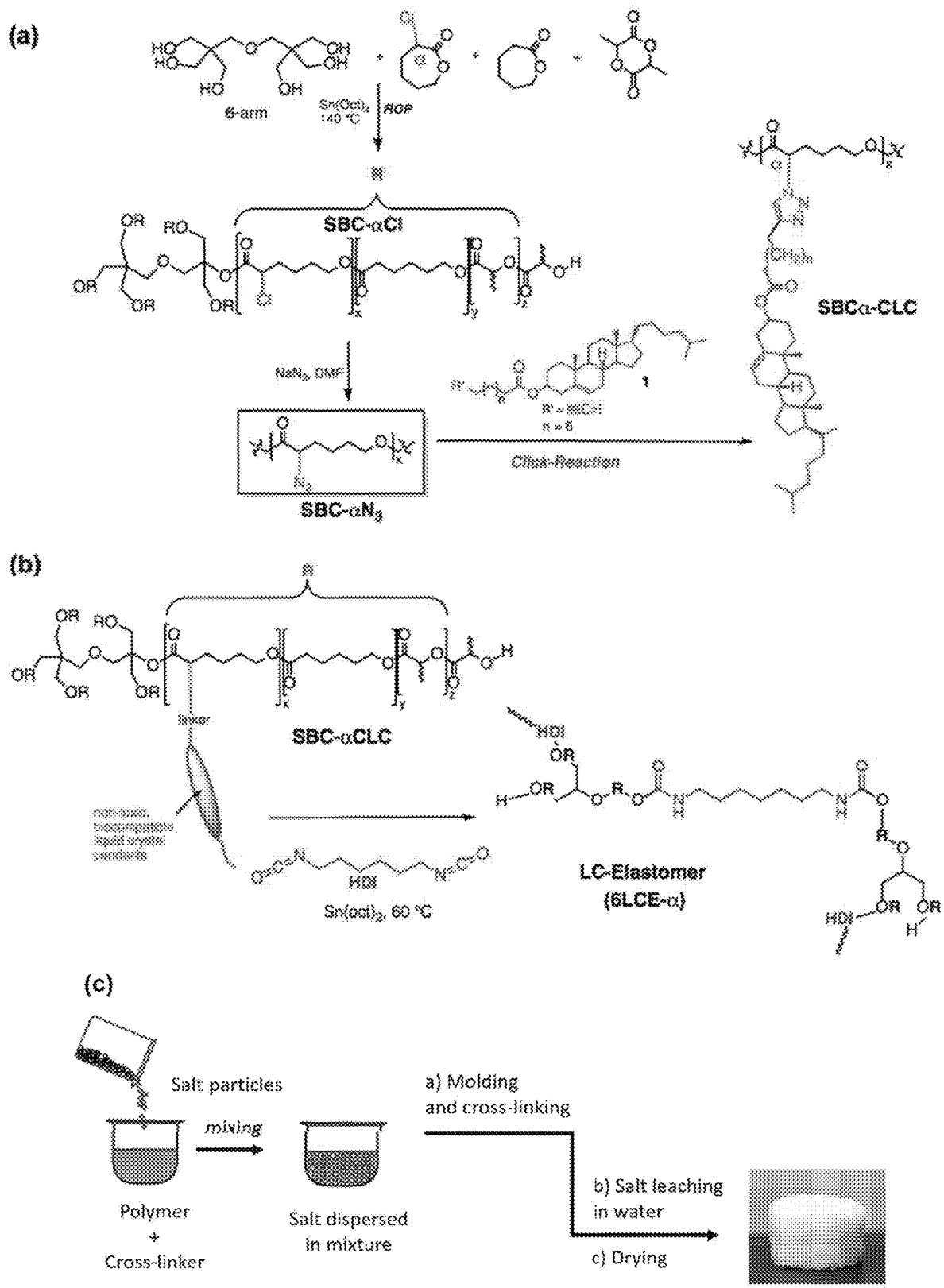
FIG. 42 - Scheme 2

BIODEGRADABLE, BIOCOMPATIBLE 3D LIQUID CRYSTAL ELASTOMERIC FOAM SCAFFOLDS HAVING TAILOR-MADE ANIMAL (HUMAN) PORE CELL SIZES VIA A SALT LEACHING METHOD ARE CAPABLE OF GROWING TISSUE THEREIN FOR THERAPEUTIC RECONSTRUCTION OF DAMAGED AND/OR DISEASED TISSUE OR ORGANS

FIELD OF THE INVENTION

Star block copolymers (SBC) having 3 to 8 arms are formed as a 3D foam scaffold having tailor-made pore sizes that mimic the size of actual animal and/or human tissue and/or organs. The pore sizes are made within the elastomeric foams via a particle (e.g., salt, sugar, carbonates, etc.) leaching process wherein a salt (or any other leaching particle) of a specific particle size is blended within the star block copolymers and crosslinked as by polyisocyanate compounds. Water or other suitable solvent are utilized to dissolve and leach out the salt leaving an open pore system. Animal and/or human cells are then seeded (e.g., added, placed, injected) into the 3D elastomeric foam scaffold that contains pendant liquid crystals groups (that will promote anisotropy to the SBC and final elastomer network) on the SBC whereby with the aid of nutrients, cells are formed within the pore system that are viable for at least three months. The tissue and/or cells within the elastomeric scaffold can be applied to animal and/or human tissue and/or organs whereupon they grow and reconstruct the damaged, injured, diseased, etc., area and result in a healthy, repaired, and viable tissue or organ. The elastomeric liquid crystal containing foam scaffold will degrade naturally and/or also be consumed by the growing cells so that it no longer exists.

BACKGROUND OF THE INVENTION

US 2016/0046761 relates to controlled biodegradable smart responsive scaffold (SRS) materials that enhance attachment and viability of cells, i.e. actively guiding their expansion, proliferation and in some cases differentiation, while increasing their biomechanical functionality. The same is an important key issue for tissue regeneration. Chemically build-in functionality in these biodegradable SRS materials is achieved by varying structural functionalization with biocompatible liquid crystal motifs and general polymer composition allowing for regulation and/or alteration of tensile strength, surface ordering, bio-adhesion and biodegradability, bulk liquid crystal phase behavior, porosity, and cell response to external stimuli. Liquid crystal modification of such polymeric scaffolds is an ideal tool to induce macroscopic ordering events through external stimuli (in some cases without external stimuli).

An article by SHARMA, A. et al, titled "Biocompatible, Biodegradable and Porous Liquid Crystal Elastomer Scaffolds for Spatial Cell Cultures", Macromol. Biosci. 2015, pp. 200-214, Vol. 15 relates to a report on the modular synthesis and characterization of biodegradable, controlled porous, liquid crystal elastomers (LCE) and their use as three-dimensional cell culture scaffolds. The elastomers were prepared by cross-linking of star block-co-polymers with pendant cholesterol units resulting in the formation of smectic-A LCEs as determined by polarized optical microscopy, and X-ray diffraction. Differential scanning calorimetry (DSC) helped determined glass and phase transition temperatures. Scanning electron microscopy (SEM) revealed the porosity of the as-prepared biocompatible LCEs, making them suitable as 3D cell culture scaffolds. Biodegradability studies in physiological buffers at varying pH show that these scaffolds are intact for about 11 weeks after which degradation sets in at an exponential rate. Initial results from cell culture studies indicate that these smectic LCEs are compatible with growth, survival, and expansion of cultured neuroblastomas and myoblasts when grown on the LCEs for extended time periods (about a month). These preliminary cell studies focused on characterizing the elastomer-based scaffolds' biocompatibility and the successful 3D incorporation as well as growth of cells in 60 to 150-mm thick elastomer sheets.

An article by GAO, Y. et al., titled "Biocompatible 3D Liquid Crystal Elastomer Cell Scaffolds and Foams with Primary and Secondary Porous Architecture, ACS Macro Letters, 2016, pp. 4-9, Vol. 5 relates to 3D biodegradable and highly regular foam-like cell scaffolds based on biocompatible side-chain liquid crystal elastomers have been prepared. Scaffolds with a primary porosity characterized by spatially interlaced, interconnected microchannels or an additional secondary porosity featuring interconnected microchannel networks define the novel elastomeric scaffolds. The macroscale morphology of the dual porosity 3D scaffold resembles vascular networks observed in tissue. 3D elastomer foams show four times higher cell proliferation capability compared to conventional porous templated films and within the channels guide spontaneous cell alignment enabling the possibility of tissue construct fabrication toward more clinically complex environments.

Synthesis of Biocompatible Liquid Crystal Elastomer Foams as Cell Scaffolds for 3D Spatial Cell Cultures. J. Vis. Exp. (122), e55452, doi:10.3791/55452 (2017).

SHARMA, A. et al, titled "Effects of Structural Variations on the Cellular Response and Mechanical Properties of Biocompatible, Biodegradable, and Porous Smectic Liquid Crystal Elastomers", *Macromol. Biosci.* 2017, article number 1600278, Vol. 17.

SUMMARY OF THE INVENTION

Tissue regeneration requires a three-dimensional (3D) smart materials as scaffolds for transport of nutrients. Biodegradable and biocompatible liquid crystal containing elastomers are utilized to create dynamic substrates for cell culture. The scaffolds comprise lactone and lactide-based star block copolymers having generally a cholesterol-based liquid crystal as a side-group. The scaffold material is blended with salt crystals of a specific desired size and crosslinked as by polyisocyanates to obtain liquid crystal elastomers that have a porous tailor-made architecture once the salt is removed by leaching with water or other suitable solvent. The specific pore size structures of the 3D elastomeric scaffolds are utilized to mimic native environments that promote cell attachment, growth, proliferations, and in some cases cell differentiation. The elastomeric scaffolds can be specifically sized, such as a bandage, and applied to a damaged or diseased tissue and/or organ whereby cells grow thereon and repair the damaged or diseased area. Since the scaffold is biodegradable (degradation rate can be tailored to specific needs), it will be naturally consumed, and disappear within a matter of days after application thereof to a human. The type of cells that can be grown and repaired in an animal or human body are many and include red blood cells, hepatocytes, brain cells, endothelia cells, adult mammalian skin cells, smooth muscle cells, osteogenic cells, human skin fibroblasts, fat cells, stem cells and any other somatic cells in general.

An elastomeric foam scaffold for cells, comprising: a one or more elastomeric star block copolymers having at least one arm containing one or more pendant cholesteric or a fluorinated cholesteric liquid crystal thereon; wherein said one or more elastomeric star block copolymers are crosslinked by a polyisocyanate; and wherein said elastomeric liquid crystal foam scaffolds has a predetermined internal pore morphology derived from a solvent soluble salt or a solvent soluble sugar.

A method for forming a polymeric cell scaffold comprising the steps of: polymerizing one or more polyols having from about 3 to about 8 alcohol groups, one or more lactones containing from about 2 to about 6 carbon atoms, one or more halogenated lactones having from 2 to about 6 carbon atoms, and one or more lactides and forming a star block copolymer having from 3 to about 8 arms, reacting said star block copolymer with a liquid crystal moiety and forming a liquid crystal containing star block copolymer; mixing said liquid crystal star block copolymer with a soluble salt, or a soluble sugar, or both, and with at least one polyisocyanate crosslinking agent; and curing said components and forming a polymeric foam scaffold.

DESCRIPTION OF THE DRAWINGS

The patent of application file contains at least one drawing executed in color. Copies of this patent or patent application publication with color drawing(s) will be provided by the office upon request and payment of the necessary fee.

The invention will be better understood and other features and advantages will become apparent by reading the detailed description of the invention, taken together with the drawings, wherein:

FIG. 13 shows biodegradable, biocompatible LC elastomers; smectic LCEs based on star block co-polymers;

FIG. 15 relates to a brief description of tissue engineering and to the soft tissue elasticity (i.e. tensile strength) as well as to the optimum pore size of various types of human tissue, muscles, or organs;

FIG. 17 shows, that all LCEs prepared independently of the initiator used, or the position of the pendant LC (alpha or gamma) produced SmA LCEs;

FIG. 19 shows, Primary Dermal Fibroblasts (hDF) were grown on LCE films. Cells aligned within the LCEs showing high anisotropy, before inducing any external stimuli to the LCE. C2C12 Myoblasts (muscle cells) were used to test viability on the LCEs, cells grew preferring the 4LCE-alpha and 6LCE-alpha substrates;

FIG. 20 shows, that most of the mechanical properties of cells are reported, but no description of what method was used. This article from McKee et al. (Tissue Eng. B 17, 3, 155-164, 2011), demonstrates the need for clarification of mechanical testing used, whether it was indentation or tensile measurements;

FIG. 21 shows, that our elastomers tested using indentation and tensile measurements cover a wide range of mechanical properties similar to those of tissue;

FIG. 26 shows, C2C12 cells grown on LCE foams were PEG was added as initiator for a more slightly hydrophilic LCE. Cells proliferated throughout the 3D foam network for 14 days (as observed using confocal microscopy). Metabolic essay was performed of LCE film (control), LCE immersion channel foam with primary porosity and LCE foam with primary and secondary porosity. Cells preferred LCE foam with primary and secondary porosity;

FIG. 29 shows images of globular nematic LCEs, cultured scheme path is shown on top images. Bottom images show two types of globular morphologies E50 and E80 that correspond to two different ratios of surfactant in water vs toluene, demonstrating that the amount of surfactant can affect the morphology of the globules;

FIG. 40 shows our conclusions of work so far. How our LCEs have been developed as cell scaffolds but can also host several other types of materials including the creation of metamaterials. Figure represent our work where cells are grown on: A 7 D LCE foams; B globular LCEs; C, E, F, & G film LCEs;

FIG. 41 shows a schematic as to the preparation of the elastomeric star block copolymer; and FIG. 42 relates to the cultured pathway followed for the preparation of LCEs wherein polyisocyanates were used as crosslinking agents.

DETAILED DESCRIPTION OF THE INVENTION

Figure 1:
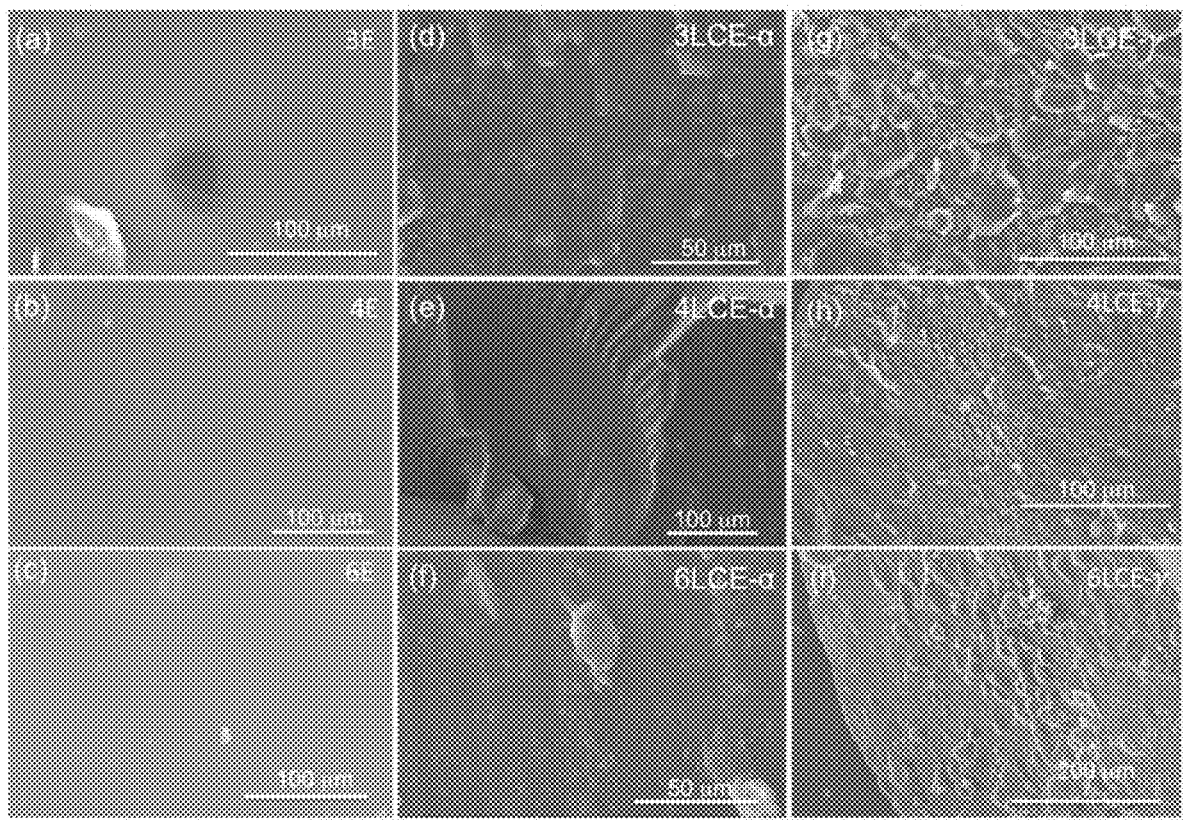
FIG. 1 is SEM images showing the internal morphology of a) 3E, b) 4E, c) 6E films, d) 3LCE-α, e) 4LCE-α, f) 6LCE-α, g) 3LCE-γ, h) 4LCE-γ, and i) 6LCE-γ.

Cultured and bioinspired cellular scaffolds can promote the development of the biophysical and biochemical environment of seeded cells called the extra cellular matrix (ECM). The ECM is a complex and dynamic system consisting of biomacromolecules that surround the cells and governs the cellular behavior including cell differentiation, proliferation, migration, viability, and other specific functions. Cultured biodegradable polymers based on poly($\varepsilon$-caprolactone), poly(lactic acid), poly(glycolide), poly(p-dioxanone), poly(carbonates), and poly($\alpha$-amino acids) as well as copolymers made of these building blocks are utilized. Key advantages of these materials are the possibilities to easily tailor their chemical and mechanical properties as well as biodegradation simply by introducing small changes in their chemical compositions.

Liquid crystals (LCs) have intrinsic anisotropic properties making them ideal candidates to be incorporated within cell scaffold systems. In this respect, especially liquid crystal elastomers (LCEs) present a unique example of a combination between LC properties and elastic polymer response. LCEs are a special class of soft materials featuring orientational order, stimuli responsive shape changes as well as elasticity. LCEs have found applications in photo-responsive devices, LC gels, as artificial muscles, and actuators. 3D channel or foam-like as well as globular morphology are viable candidates for active cell scaffolds that support the attachment and proliferation of cells, further expanding possibilities toward tissue regeneration.

Smectic cholesterol functionalized P-$\varepsilon$-CL/(D,L)-LA cross-linked star block-copolymers can be utilized, where the position of the cholesterol pendant group was varied ($\alpha$ or $\gamma$ to the CL, i.e. crosslinked, carbonyl group). These LCE scaffolds are intrinsically porous exhibiting "Swiss-cheese" morphology, permitting both the attachment and profile ration of various cell lines such as neuroblastomas and skeletal muscle cells (myoblasts).

Thus, the synthesis and characterization of new series of smectic LCE cell scaffolds was utilized based on cross-linked star block copolymers (SBC) with 3-arm, 4-arm, and 6-arm central nodes, adjusting simultaneously the connectivity and the degree of cross-linking between individual polymer strands. These architectural handles allow custom-modify to the mechanical properties of these LCEs by one simple cultured variation to values closely matching those of various tissues of interest, along with promoting superior and stimuli-responsive surface properties for cell attachment. Cholesterol-based moiety was selected as the LC pendant in the system due to both its mesogenic nature bioactive role in cell membranes and occurrence in biological tissues. The data herein will focus particularly on the surface and mechanical properties and their impact on cell response of these LCEs with 3-arm, 4-arm, and 6-arm networks with variable elasticity. In addition, we continued to vary the position of the LC pendant group. To prepare 3-arm-LCEs-α/γ, 4-arm-LCEs-α/γ, and 6-arm-LCEs-α/γ, glycerol (3-arm), pentaerythritol (4-arm), and dipentaerythritol (6-arm) were used as central nodes (as well as initiators), respectively (see Scheme 1 for structures and synthesis). The obtained elastomers (3LCE-α, 3LCE-γ, 4LCE-α, 4LCE-γ, 6LCE-α, and 6LCE-γ) were fully characterized and then tested with respect to their mechanical properties, biocompatibility and cell viability in cell cultures using mouse skeletal myoblasts (C2C12) and human dermal fibroblast (hDF) cell lines.

The elastomeric star block copolymers of the present invention contain liquid compounds made as follows and as set forth in Scheme 1.

Scheme 1. a) Chemical structure of 3-arm, 4-arm, and 6-arm initiators (central nodes) and b) synthesis pathway to star block copolymercholesterol liquid crystal (SBCα-CLC) (showing a purple link) and SBCγ-CLC (showing a pink link). The ratio of all caprolactones to D,L-lactide is 1:1; the ratio between LC-modified and nonmodified caprolactone is 1:10. c) Crosslinking with bis-caprolactone (BCP) to obtain a 3-arm alpha (or gamma) positioned LCE. For abbreviations of LCEs see Table 1.

TABLE 1

Names of elastomers samples studied.

| Sample | Elastomer name[a] |
|---|---|
| Unmodified elastomers | 3E |
| | 4E |
| | 6E |
| α-series | 3LCE-α |
| | 4LCE-α |
| | 6LCE-α |
| γ-series | 3LCE-γ |
| | 3LCE-γ |
| | 3LCE-γ |

[a] Arabic numbers in front of elastomer name (3, 4, or 6) indicate the number of elastomer arms of the central node (initiator). Alpha (α) or gamma (γ) series indicate position of the LC triazole moiety with respect to the caprolactone carbonyl group.

All air sensitive manipulations were carried out under nitrogen gas. ε-caprolactone (ε-CL, from Alpha Aesar) was dried over calcium hydride and distilled under reduced pressure. Glycerol, cholesterol, pentaerythritol, dipentaerythritol, triethylamine, stannous 2-ethylhexanoate, chromium (VI) oxide, sodium sulfate, pyridinium chlorochromate, and sodium bicarbonate were used as received (Sigma-Aldrich). Sodium thiosulfate purchased from Fisher Scientific was used as received. 3-Chloroperbenzoic acid (m-CPBA, from Sigma-Aldrich) was dissolved in diethyl ether and this ether solution was washed with a buffer solution (prepared from 1.28 g sodium phosphate monobasic monohydrate and 8.24 g sodium phosphate dibasic heptahydrate in 800 mL distilled water at pH=7.4). All solvents used for the synthesis and purification were EMD Millipore grade purified by a Pure-Solv solvent purification system (Innovative Technology Inc.). Dulbecco's modified Eagle medium (DMEM) with 4.5 g $L^{-1}$ glucose and sodium pyruvate without L-glutamine and Dulbecco's phosphate buffered saline (PBS) without calcium and magnesium were purchased from Corning CellGrO. Penicillin streptomycin solution (Pen-Strep) was purchased from Thermo Scientific. Fetal bovine serum (FBS) and trypsin were purchased from HyClone. Formaldehyde solution for molecular biology, 36.5%-38% in $H_2O$ was purchased from SIGMA Life Science. CyQuant Cell Perforation Assay Kit, 4',6-diamidino-2-phenylindole (DAPI), UltraPure Agarose were purchased from Invitrogen. Reagent Alcohol 200 proof ACS Grade (Denatured Ethanol) was purchased from VWR. Mouse skeletal cell line (C2C12) and human primary dermal fibroblast normal cells (hDFs) were purchased from American Type Culture Collection.

Property Testing of LCEs.

$^1$H Nuclear Magnetic Resonance (NMR), $^{13}$C NMR, and Fourier Transform Infrared Spectroscopy (FT-IR). Proton and carbon NMR spectra of copolymers were recorded in $CDCl_3$ at room temperature on a Bruker DMX 400 MHz instrument and referenced internally to residual peaks at 7.26 ($^1$H). Infrared spectroscopy of polymers was recorded using a Bruker Vector 33 spectrometer equipped with attenuated total reflection (ATR) mode.

Thermal Properties of SBCs and Final Elastomers. Differential scanning calorimetry (DSC) was used to obtain glass transition temperatures of the star block-copolymers and LC elastomers. Thermal phase transitions were recorded with a Thermal Perkin Elmer Pyris1 analyzer with a scanning rate of 10° C. min-1 from −70 to 250° C. under a nitrogen atmosphere. Thermal degradation studies were carried out with Hi-Res thermal gravimetric analysis (TGA)-2950 thermal analyzer under nitrogen atmosphere with ramp of 10° C. min-1.

Morphology of Elastomers

Scanning electron microscopy (SEM) was used to visualize and study elastomer morphology. All samples were freeze fractured (to study the internal morphology) and then gold coated (700 Å) using a sputter coater (Hummer VI-A, Anatech Ltd.) at 10 mA DC for 3 min and images were acquired using a Hitachi S-2600N SEM.

Small-Angle X-Ray Diffraction (SAXD) of Elastomers

SAXD was used to determine liquid crystalline phases of liquid crystal modified copolymers and elastomers (LCEs). SAXD data were data collected at the X-ray Operations and Research Beamline 12-ID-B at the Advanced Photon Source, Argonne National Laboratory for unmodified elastomers. For γ-LCEs, SAXD data were collected at beamline 7.3.3 of the Advanced Light Source (ALS) at Berkeley. Samples at the ALS were mounted on a TST350 Linkam tensile stage.

Optical Microscopy

Polarized optical microscopy (POM) was performed using an Olympus BX53 polarizing microscope (20×) equipped with a Linkam LTS420 heating/cooling stage. All samples were initially heated to the isotropic liquid phase and then cooled to observe the temperature range at a rate of 0.1° C. Fluorescence confocal microscopy was carried out using an Olympus FV1000 equipped with three laser lines and ImageJ was used for image analysis/processing. Fluorescence for cell proliferation was measured using a Molecular Devices M4 SpectroMax Multi-Mode Microplate Reader.

Mechanical Testing of Elastomers

Uniaxial tensile testing (Zwick/Roell Z0.5, 100 N load cell) was performed under ambient conditions at a strain rate of 40% min$^{-1}$ on solvent-cast elastomeric films. A modified version of ASTM D1708 was utilized for testing with the dimensions scaled down by a factor of two due to limited sample quantity. Five tensile samples per elastomer were examined for mechanical response; each sample was held between Mylar sheets during cutting to relieve stress concentrations along the sample edges. The elastic modulus (E) was determined from the slope of the stress-strain curve between 0.10% and 0.35% strain.

Contact Angle Measurements

Static water contact angle (WCA) measurements were completed using a CAM 200 optical contact angle meter (KSV Instruments LTD). The WCA value was acquired by forming single water drop at the tip of the syringe, bringing the sample up to the drop, and pulling it away on the sample. The drop was then allowed to achieve equilibrium on the sample by waiting two minutes. Contact angles were collected and averaged from two separate drops per sample using KSV CAM 2008 software.

An object of the present invention is to create 3D porous LCE foam as a host scaffold for brain cells with capability to become a stimulated substrate. However it can be used for any stem or somatic cell in the body, by adjusting a few parameters (such as biodegradability, mechanical properties, pore size, and density among others) depending on the monomer ratio, initiator type and crosslinker. Neurons and glial cells are major cell types of the central nervous system: The viability and expansion of cells is governed by constitutive parameters of the scaffold, such as porosity as well as stiffness of substrate to which the cells are adhered that need to be controlled.

Scheme 2 shows the cultured pathway followed for the preparation of LCEs wherein polyisocyanates were used as crosslinking agents. The mechanism is based on a random ring opening polymerization of dipentaerythritol as the 6-arm initiator, ε-caprolactone (ε-CL), modified ε-caprolactone (α-chloro-ε-caprolactone (α-Cl-ε-CL), and (D,L)-lactide (D,L-LA) (Scheme 2a). Other components can be any α-halide-ε-Caprolactone, γ-halide-ε-Caprolactone, and L-lactide. In this reaction, tin(II) 2-ethylhexanoate is used as a catalyst to obtain 6-arm star block-copolymer (6SBC-αCl). Substitution of the halogen atom (—Cl) by an azide group (—N3), named as 6SBC-αN3, permits the covalent attachment of a liquid crystal moiety such as modified cholesterol (LC) as pendant to the polymer backbone using a 5-members ring through alkyne-azide Huisgen's cycloadditon reaction ("click" reaction). Click reaction produces a five member ring linker of the LC to the polymeric unit. Cholesterylhexynoate is chosen as the LC unit, due to its cholesterol-based nature conferring biocompatibility. 6SBC-αCLC was characterized by proton Nuclear Magnetic Resonance (1H NMR) and Fourier-Transform Infra Red spectroscopy (FTIR). The LC moiety can also be attached using a atom transfer radical addition (ATRA), conditions. This ATRA method enables us to have a less steric constraint (lack of five member ring link produced during click reaction) of the LC moiety to the polymeric backbone, adding mobility/flexibility to the LC pendant.

Scheme 2. Synthesis pathways for scaffolds, e.g. liquid crystal of star block-copolymer with cholesterol liquid crystal pendants: a) 6SBC-αCLC. The ratio of all caprolactones to D,L-lactide is 1:1; the ratio between chlorine-modified and non-modified caprolactone is 1:10, b) 6LCE-α. The ratio between 6SBC-αCLC and the cross-linker is 4:1.0, and c) the ratio between salt and 6SBC-αCLC is 40:1 for foam preparation procedure.

The Scheme 2(a) cultured transformations were followed by ATR (attenuated total reflection) FT-IR spectroscopy, i.e. by the appearance of the 2100 cm$^{-1}$ band corresponding to the displacement of the chloro by an azide group. This substitution is further confirmed by $^1$H NMR spectroscopy considering the higher chemical shift of the proton bound to the same carbon atom as the azide group. The attachment of the LC pendant to the SBC was confirmed by FT-IR, i.e. by the disappearance of the 2100 cm$^{-1}$ band and the appearance of a new band at 3260 cm$^{-1}$ corresponding to the presence of a triazole ring. The formation of the triazole ring was also indicated by the presence of a singlet observed at 7.31 ppm in $^1$H NMR spectra. For the ATRA procedure, we follow the proton formation via $^1$H NMR at 3.5 to 4.4 ppm, preferably at 3.98 ppm only.

Synthesis and Morphology of LCE to AM.

With respect to the various reactants, they are various monomers. One such type of monomer are polyols are branched in order that a star block copolymer can be made therefrom. Number of branch or alcohol groups or arms containing at least 3 to about 8 (hexaglycerol), with 3, 4, or 6 arms being preferred as set forth in Scheme 1. Examples of suitable polyols include glycerol, pentaerythritol dipentaerythritol and hexaglycerol.

Another group of monomers are cyclic esters such as lactones and generally contain a total of from about 2 to about 6 carbon atoms (containing a ketone group at one of the carbons adjacent to an oxygen group) with 6 carbon atoms being preferred, such as 6-hydroxyhexanoic acid lactone. The present invention also contains one or more halide substituted lactone monomers containing from 2 to about 6 carbon atoms, wherein the halide is Br, Cl and I. Halide lactones are utilized because the halide group is very easily substituted for an azide group, the azide group plays a role on azide-alkyle Huisgen ciycloaddition reaction ("click" reaction) to attach LC units to the polymer chain. A preferred halide lactone is alpha-bromo ε-caprolactone as well as gamma-bromo-ε-caprolactone.

A preferred halide lactone is alpha-bromo ε-caprolactone as well as gamma-1-bromo-ε-caprolactone.

Another component in the formation of the star block copolymer of the present invention is one or more lactide monomers, i.e. D,-L-lactide or L-lactide.

The star copolymers of the present invention are made by reacting the above-noted polyols having three or more hydroxyl groups, one or more lactones, one or more halide, substituted lactones, or one or more lactides in the presence of a catalyst to obtain a star block copolymer wherein the number of arms are that of the polyol. The length of each arm of course will depend upon the number of moles of the lactone, etc., utilized. Suitable catalysts include tin(II) 2 ethylhexanoate or dimethylmethoxyborane with tin(II) 2 ethylhexanoate being preferred. Desirably, the lactone branch can contain randomly about 20% to about 45% repeat units with 30% to about 35% being preferred. The number of random repeat units of the halides substituted lactone is about 20% to about 45% with 30% to about 35% being preferred. The number of random repeat units of the lactide block is about 20% to about 45% with 30% to about 35% being preferred. The above ranges are based on the total number of all repeat units in the star block copolymer. Polymerization is carried out at from about 80° C. to about 160° C. and preferably from about 125° C. to about 140° C.

If mixed together for example: α-chloro-ε-caprolactone (α-Cl-ε-CL), ε-caprolactone, and D,L-lactide, after ring opening polymerization we obtained star block copolymer SBC-α-Cl. Then the halide group (chlorine) is replaced by an azide (—N$_3$) group, the SBC is now SBC-α-N$_3$. After that, using click reaction, then we "click" the cholesterol LC group, or any derivative thereof, converting the SBC into a SBC-α-CLC. The symbols represent the stages for SBC formation prior crosslinking. The whole process is repeated with γ-chloro-ε-caprolactone (γ-Cl-ε-CL), ε-caprolactone, and D,L-lactide, forming first SBC-γ-Cl, then SBC-γ-$N_3$, then SBC-γ-CLC.

As set forth in Schemes 1 and 2, subsequently a non-toxic, biocompatible liquid crystal is attached to the star block copolymer to one or more of the halide substituted lactone blocks. An amount of liquid crystal is utilized so that the number of liquid crystals desirably is high, for example from about 60% to about 100% and desirably from about 80% to about 100% replacement of all pendant halide groups. Suitable biocompatible liquid crystals include cholesteric, cholesterol-based chiral nematic liquid crystals or any derivative thereof, or any cholesteryl liquid crystal or derivatives thereof such as cholesteryl-5-hexynoate, or sulfonated cholesteryl liquid crystal, or any 3,4-difluorophenyl-bicyclohexyl-based nematic liquid crystals or any derivative thereof. Examples of fluorinated chlosteric liquid crystals including TL203 and TL205 produced by Merck. The reaction is known to the art and to the literature and generally involves direct substitution of the cholesteric liquid crystal for the halide compound. The formation of the above-noted cholesteric containing liquid crystal, star block copolymer as well as specific liquid crystals are set forth in U.S. patent application Ser. No. 14/783,892 filed Oct. 12, 2015, hereby fully incorporated by reference. Alternatively, the star block copolymer can have a pendant chain or block that contains one or more fluorinated cholesteric liquid crystal thereon that exists in addition to one or more cholesteric liquid crystals on the same chain.

Subsequent to the formation of the liquid crystal containing block copolymers of the present invention, such block copolymers are crosslinked by a polyisocyanate having from about 2 to about 5 isocyanate groups. Hexamethylene diisocyanate (HDI) (Scheme 2b) was chosen as the crosslinker (forming urethane linkages) because of its low processing temperature. Examples of other suitable polyisocyanate crosslinking agents including HDI, TDI, toluene diisocyanates, MDI, methyl diphenyl diisocyanates such as 4,4'-diisocyanates, IPDI, isophorone diisocyanates, and any combination thereof. Other diisocyanates include blocked aromatic and aliphatic polyisocyanate crosslinkers based on HDI, TDI, MDI, and IPDI, or any combination thereof. Many of such polyisocyanate crosslinking agents are produced under the trademark DESMODUR™ by Covestro Company. The amount of crosslinking agents utilized will naturally control the crosslinking density, mechanical properties, thermal properties, anisotropic properties of the LC unit and biodegradation rates. Generally the amount of crosslinking agents utilized are from about 0.3 or 0.5 to about 2.5, and desirably from about 1.0 to about 2.5 moles per 3 moles of liquid crystal containing elastomers.

Crosslinking agents of the present invention are generally free of nickel catalysts since the same has been found not to promote suitable pore size. In other words, the present invention is free of nickel catalysts, meaning that less than 2% by weight, less than 1% by weight, or nil, that is no nickel catalysts whatsoever are utilized based upon the total weight of the star block copolymers. The crosslinked copolymers that form the cell scaffolds of the present invention can be made wherein the crosslinking occurs in a mold, via casting methods, via a spin coating, via electrospinning, 3D printing, and the like.

The above-noted block star copolymer containing various liquid crystals thereon such as cholesteric liquid crystals are flexible, rubbery, elastic, biocompatible, biodegradable, and the like. Accordingly, they are generally referred to as liquid crystal elastomers. Such elastomeric materials form a substrate i.e. a scaffold for growing cells therein. That is, such liquid crystal elastomers have pores therein as well as a total amount of porosity therein based upon the total volume of the scaffold. The pores serve as a site for growing designated cells, that is also a desired cell such as those set forth in Table 2.

It has been unexpectedly found by the present invention that when a predetermined (tailor-made) scaffold pore diameter is generally slightly larger than the size of a specific type of cell, cell growth is enhanced, allowing for cells to attach, grow, and proliferate as well as allowing for mass transport (nutrients, gases and waste) management. Such cells are referenced to as cultured cells since they are derived from cells grown within the scaffold. Table 2 relates to various different types of cells and the inherent micron (cell) size (diameter) thereof.

TABLE 2

| Type of cell | Pore (cell) size (μm) (average diameter) |
| --- | --- |
| Brain cell | 30-70 |
| Red blood cell | 1-5 |
| Hepatocytes | ~20 |
| Osteogenic cell | 100-150 |
| Adult mammalian skin cell | 20-125 |
| Smooth muscle cells | 60-150 |
| Endothelial cells | <80 |
| Human skin fibroblasts | <160 |

As apparent from Table 2, the cell sizes per se can range from about 1 to about 175 microns and even larger as up to about 250 and even 300 microns, especially for osteogenic cells.

The above tailor-made cell pore sizes are made by using a salt leaching method to create a 3D porous scaffold that promotes neuronal tissue growth. For example, this method comprises mixing a LCE-α, solvent, crosslinker, and salt in a ratio 4:2:1:160 and pouring the obtained mixture into a mold. A general suitable range of the noted compounds is from about 3.5 to about 4.5 parts by weight of said LCE, from about 1.5 to about 2.5 parts by weight of said solvent, from about 0.5 to about 2.0 parts by weight of a polyisocyanate crosslinker, and from about 60 to about 350 parts by weight of a salt. A mechanical compression was used to assure the integrity of foam and increase the pore interconnectivity of the porous scaffold. Using a diisocyanate as a crosslinker implies low crosslinking temperature, allowing LCE foams after 1 h to crosslink at 60° C. Depending upon the type of polyisocyanate crosslinker, crosslinking (curing) temperatures can range from about 10° C. to about 90° C. and desirably from about 40° C. to about 70° C. and suitable cure times range from about 30 minutes to about 20 hours. After crosslinking, the SBC becomes LCE-α foam. The salt is then removed by leaving the foam scaffold in water for about one to about 5 days with about 3 days being preferred followed by drying the foam in air (Scheme 2(c)). Such a process has been found to generally yield tailor-made pores that are substantially similar in pore diameter size to each other and to a specific pore size.

As noted, an important aspect of the present invention is that the foam scaffold morphology contains a pore size slightly larger, i.e. a "predetermined pore diameter" than that of a specific designated, desired (cultured) cell, e.g. an endothelial cell, etc. For example, a particular type of cell having a specific diameter. The "predetermined pore diameter" is the average per se cell diameter plus an additional mean average cell diameter of from about 10% to about 30%. To promote vascularization, since insufficient vascularization is synonymous with cell death in tissue-engineered constructs, the final pore size morphology was designed to have enough space for cell growth and proliferation, as well as to facilitate nutrient and oxygen diffusion and also waste removal. Hence, the reason for the extra scaffold pore diameter size of from about 10% to about 30%, desirably from about 15% to about 25% Thus, a specific type of cell can be cultured. For example, for a 50 micron cell diameter, the "predetermined pore diameter" of the scaffold is from about 55 to about 65 microns. Such sized scaffold pores (predetermined pore diameter) thus make a designated per se cultured cell that is substantially the same size as the "natural cell" e.g. an endothelial cell. In other words, according to the present invention, any specific (designated) type of a cultured cell, can be produced to have a "predetermined cell diameter" that is substantially the same size, i.e. plus or minus 5% as an independent, existing natural cell of the same type. Stated differently, a designated cultured cell is capable of being tailor-made to have a cell diameter that is substantially the same size as an identical type of cell that exists in nature. Such made or cultured cells of the present invention can be utilized for subsequent end use with regard to repairing damaged, disabled, or diseased skin, muscles, organs, and the like.

The amount of the pores or cavities within the liquid crystal elastomer scaffolds of the present invention that have a desired "predetermined pore diameter" (cell size plus 10% to 30%) is generally a majority such as from about 50% to about 95%, desirably from about 60% to about 95%, and preferably from about 75% to about 95% based upon the total number of pores within a scaffold. I.e., fully interconnected pores exist. For other particular issues where there is co-culturing or a "dual or multiple" porosity size is required, then two-to-three pore sizes will be selected and each will have a presence of certain % in the bulk. This will be determined depending on the particular cell type.

Large amounts of specific types of cultured cells having an average pore diameter essentially similar to a natural type of cell, for example an endothelial cell, can be made according to the present invention and thus have the noted advantages set forth hereinabove.

Predetermined average scaffold pore diameters are made by controlling various aspects. For example, a high surface area-to-volume ratio for interconnected porous scaffolds is directly correlated to the amount and leaching particle pore size. Thus, for any desired average pore size or diameter, a different surface area of the total pores to the volume ratio thereof can be determined with respect to various different salts. Another important controlling aspect is that the amount of salt utilized, i.e. the weight ratio of salt to a liquid crystal elastomers results in larger average pore diameters as the amount of salt is increased. With respect to obtaining a desired salt size, e.g. average salt diameter or average width-depth size, the same can be readily obtained from a manufacturer. Also, the desired salt size can be obtained simply by screening a desired type of salt, for example, sodium chloride, to obtain a predetermined diameter that is slightly larger than the desired cell size, i.e. from about 10% to about 30% larger so that the formed scaffold has a desired predetermined average pore diameter. Thus, the present invention has found that star block copolymers containing liquid crystals therein can be tailor-made with regard to predetermined average pore sizes.

The porosity of the liquid crystal elastomers scaffolds of the present invention is also important and a desired porosity, i.e. total pore space of the scaffold is high, is from about 65% to about 95%, and desirably from about 70% to about 90% total pore volume based upon the total liquid crystal elastomer scaffold volume. The pores preferably are fully interconnected. The determination of such porosity values as well as the main pore values are well known to the art and to the literature.

The porosity of the liquid crystal elastomer scaffold can be varied as by changing the polymer ratio to salt ratio. As long as the final elastomer has fully interconnected pores, i.e. an open pore network.

By way of review, an important aspect of obtaining a suitable scaffold pore size is the use of one or more salts or one or more sugars, or both, that have a crystal size that is substantially similar to the desired scaffold, pore size. As previously stated, if a desired cell size of about 50 microns is desired, a salt having a crystal size of slightly larger than 50 microns must be utilized including an additional about 10% to about 30% average pore diameter. Thus, a total average diameter of the crosslinked LCE scaffold pore size of from about 55 to about 65 microns is utilized.

Generally any salt or sugar can be utilized that are soluble in a solvent such as an alcohol or other solvents such as glycols, and water, with water being highly preferred. Suitable salts include soluble salts of alkali metals, ammonium salts, halide salts, carbonate salts and sulfate salts (as long as they are biocompatible), or any combination thereof. Suitable soluble sugars include glucose, fructose, sucrose, or any combination thereof, and others with glucose being preferred.

Generally, the method for preparing the tailor-made liquid crystal elastomer scaffolds of the present invention comprises mixing the above-noted amounts of a liquid crystal elastomer, suitable amounts of a polyisocyanate crosslinking agent, and suitable amounts of a salt having a desired crystal size and pouring the mixture into a mold. The mold is then heated to a sufficient crosslinking temperature whereupon a liquid crystal elastomer foam is formed. Thereafter, the foam matrix is removed from the mold and placed in water with a sufficient amount of time until the salt crystals have been dissolved and leached out. Thereupon, the foam is dried and ready to have a desired type and size of cell inserted therein.

Figure 14:
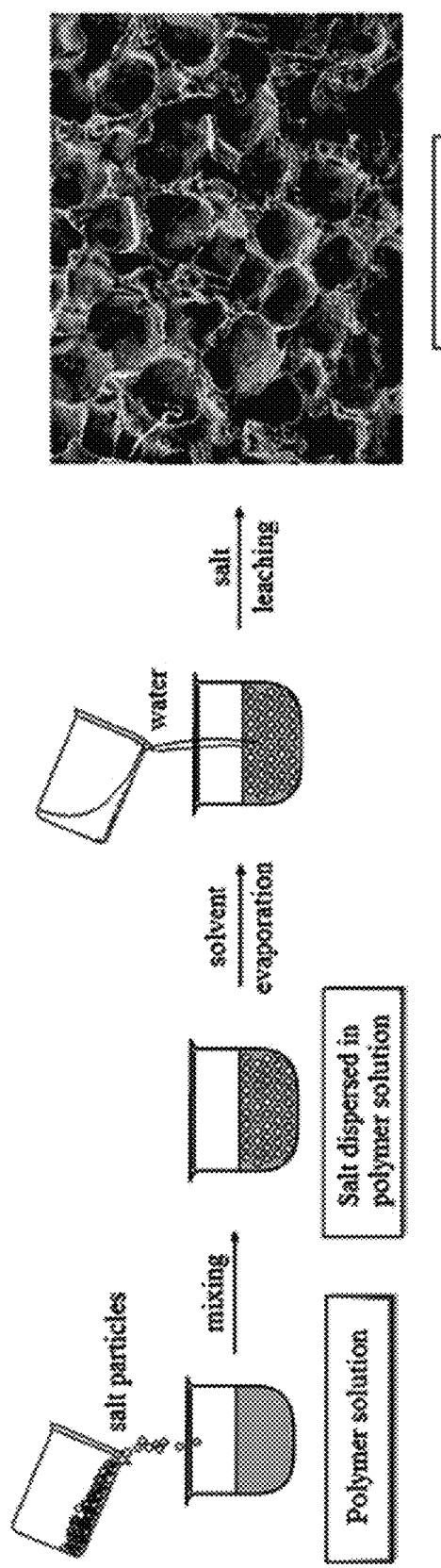
FIG. 14 shows LCE foam—salt leaching method.
Figure 16:
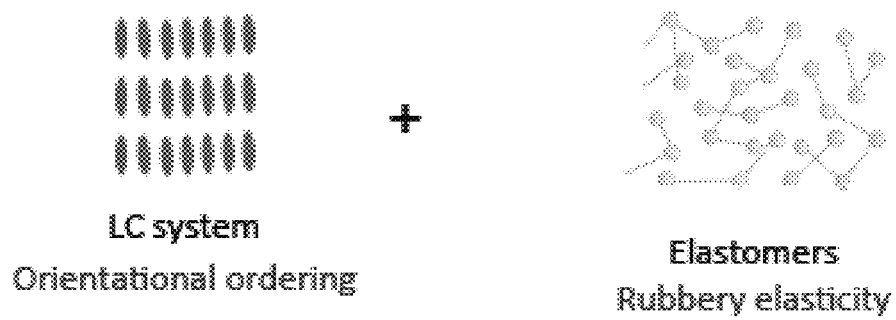
FIG. 16 shows, how the properties of LCs (orientational ordering) can be mixed with the properties of elastomers (elasticity) to produce Liquid Crystal Elastomers.
Figure 18:
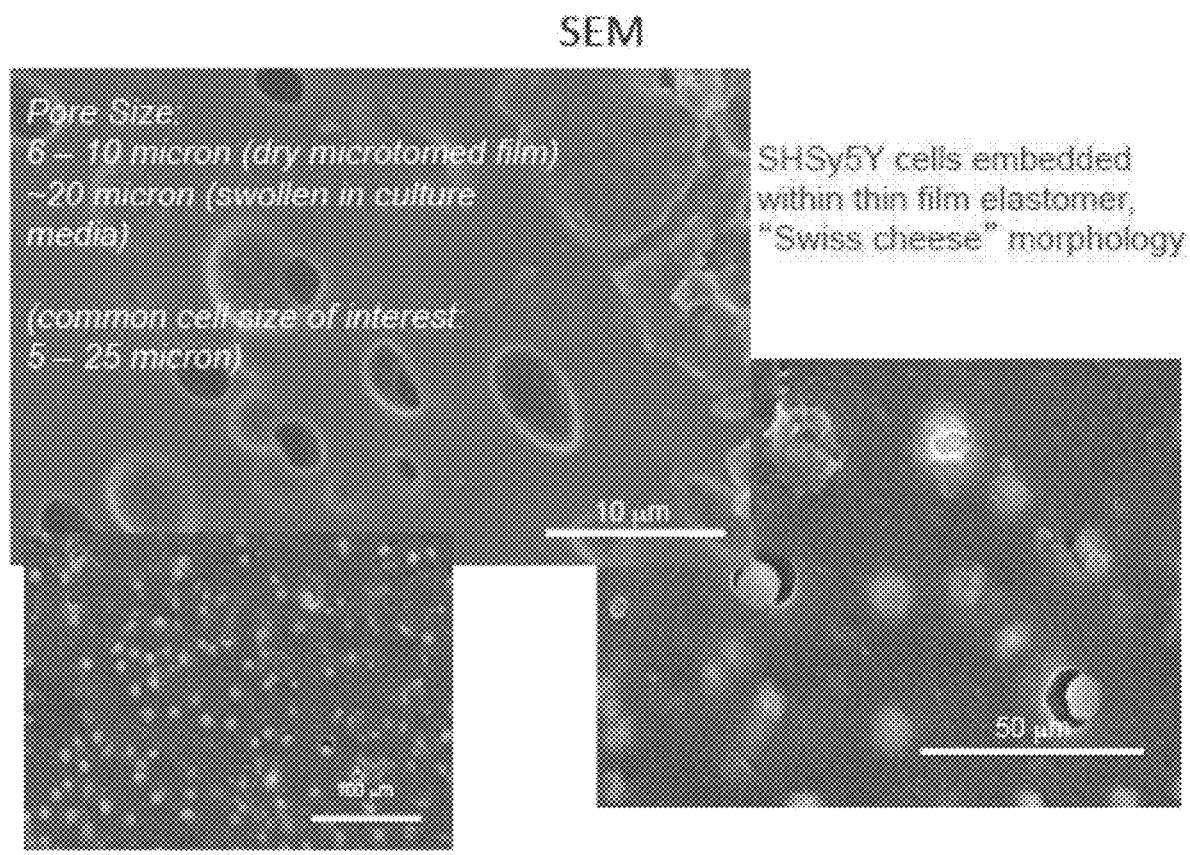
FIG. 18 shows, LCE films produced had an inherent porosity, giving a "Swiss-cheese" like structure. Cells infiltrated throughout the LCE film. However porosity in this case is not fully interconnected.
Figure 22:
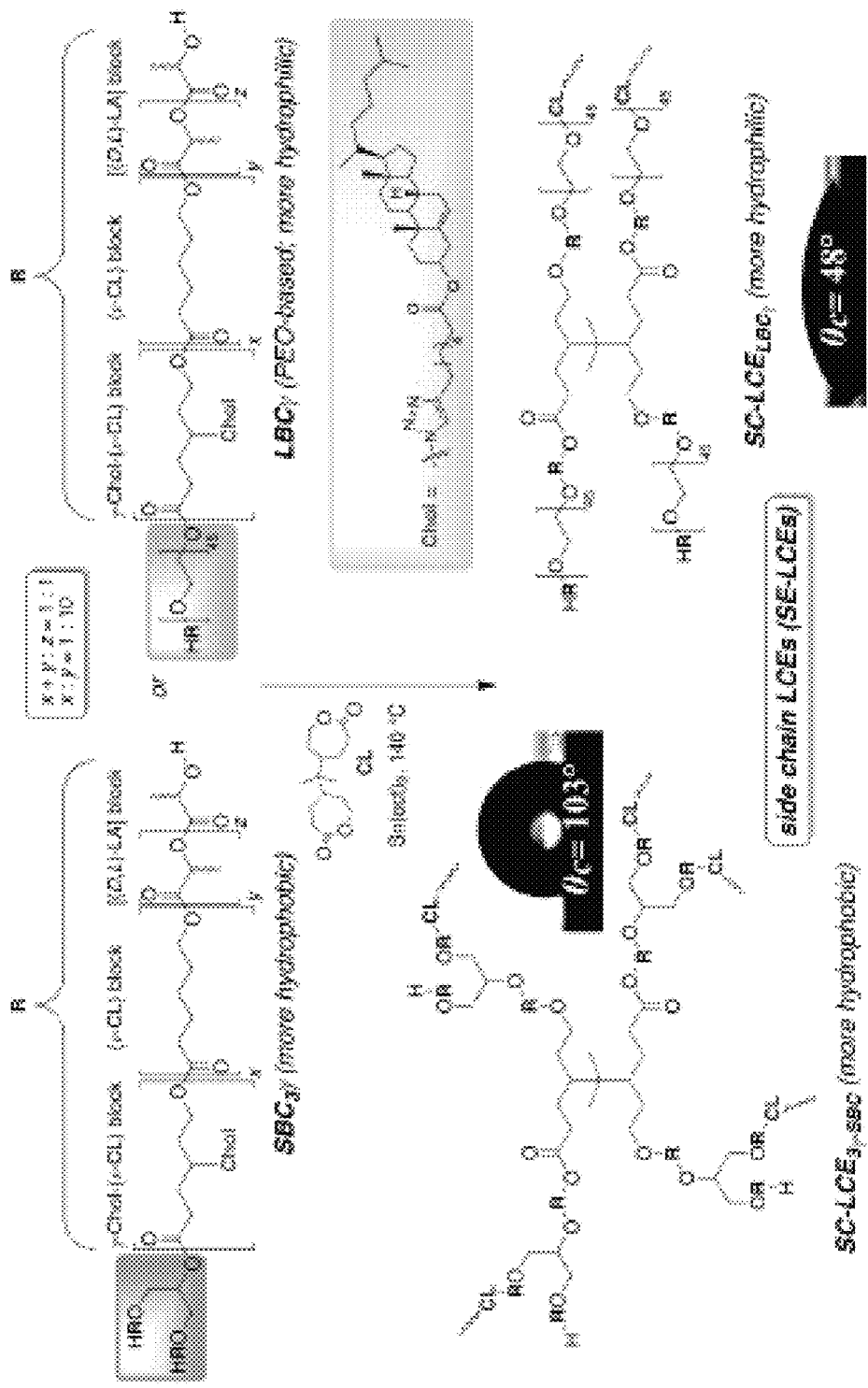
FIG. 22 shows, that we are capable of tuning the hydrophobic/hydrophilic balance of LCEs by adding/or replacing one of the initiators with PEG, making the final LCEs more hydrophilic or more hydrophobic to any degree a particular cell will require.
Figure 23:
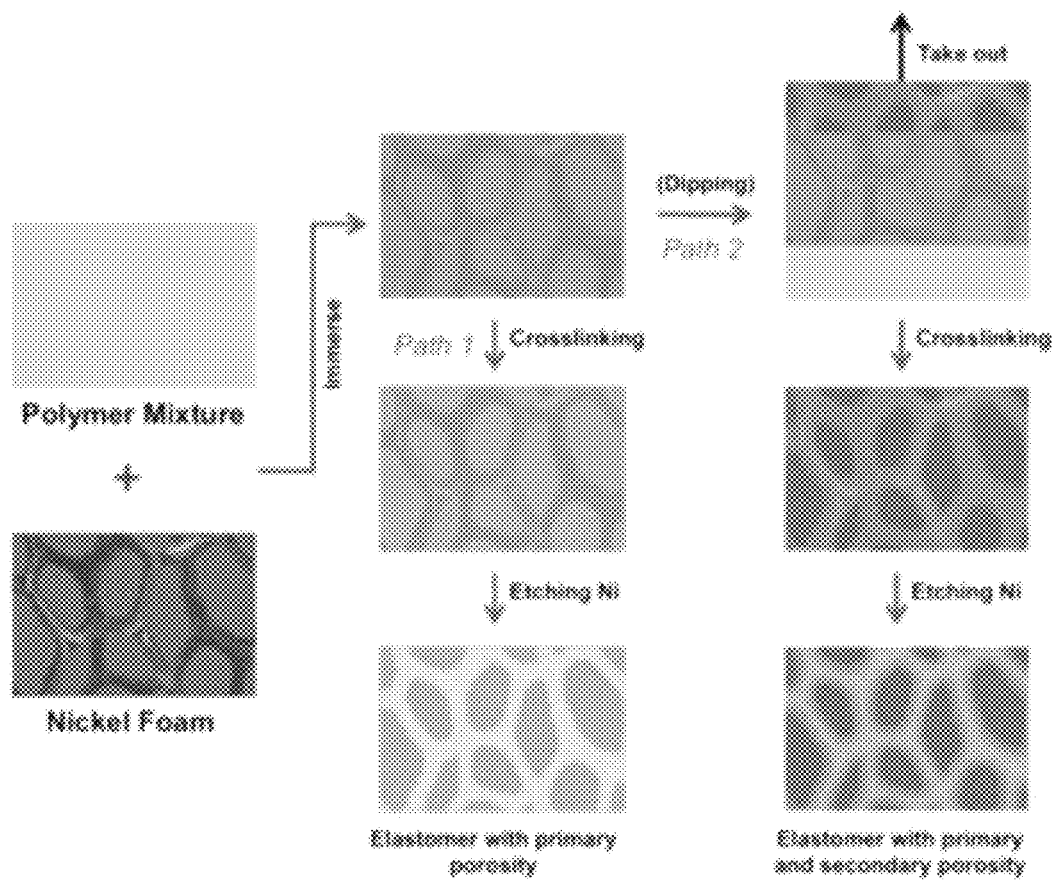
FIG. 23 shows, two paths for the creation of LCE foams, by full immersion or dipping, using nickel foam template. Nickel foam will be etched out once the crosslinking procedure has been completed.
Figure 24:
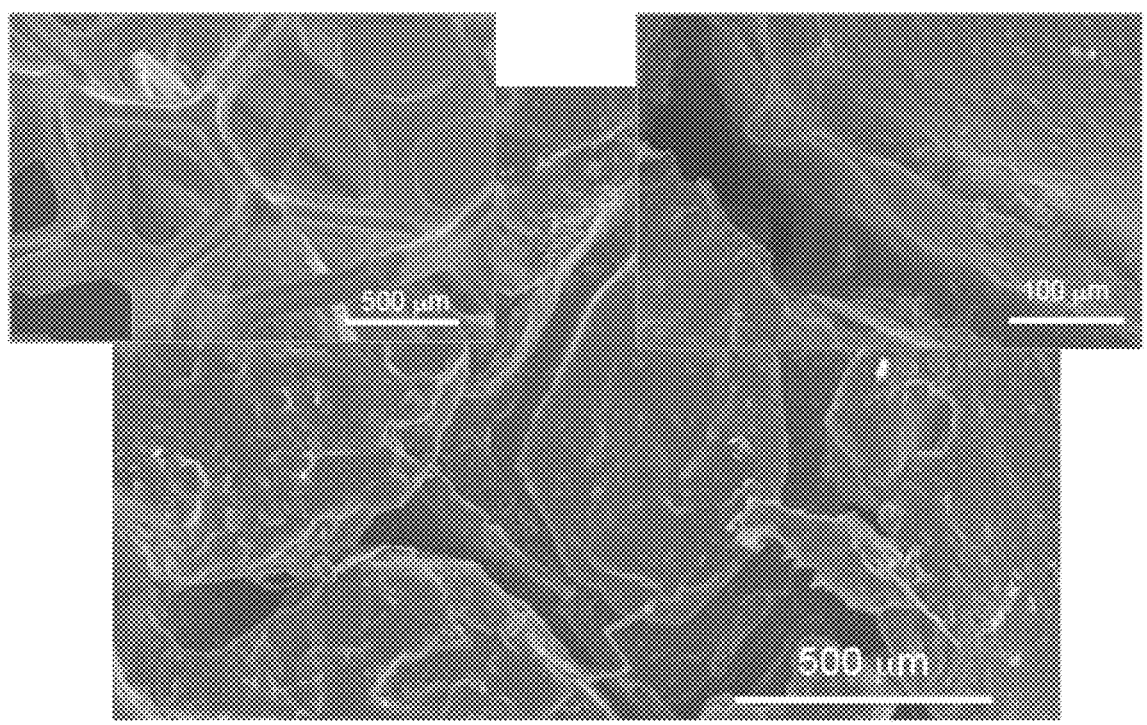
FIG. 24 shows, the LCE obtained using full immersion method. Channels/tunnels formed can be observed using scanning electron microscopy (SEM), indicating also fully interconnected pores, in a primary porosity matter (only channels or tunnels)
Figure 25:
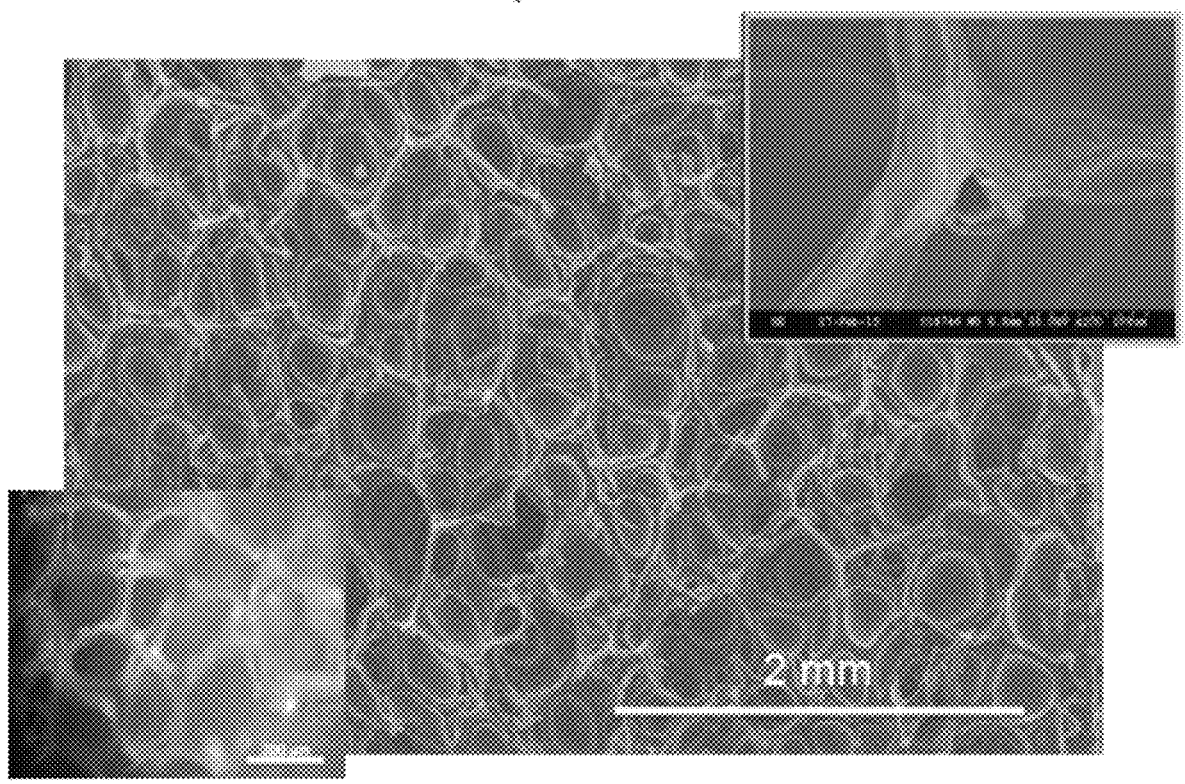
FIG. 25 shows, the LCE obtained using dipping method, LCE foam. Struts are also hollow and can be observed using scanning electron microscopy (SEM), indicating also fully interconnected pores, in a primary and secondary porosity matter (hollowed struts). Inset on right shows that struts are hollow. Inset on bottom left show an optical image of LCE foam.
Figure 27:
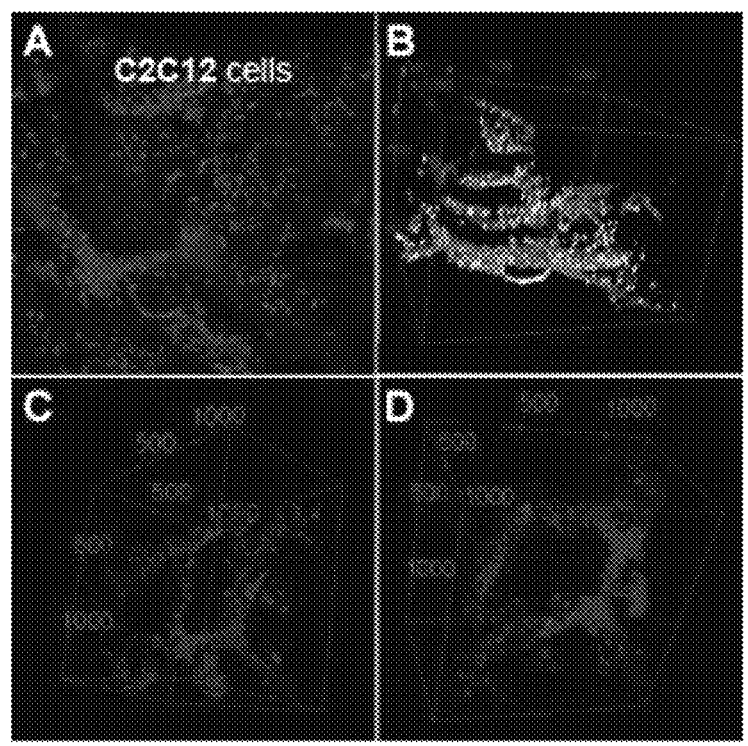
FIG. 27 shows, confocal microscopy of 3D views from different angles, of C2C12 cells grown on LCE foams.
Figure 28:
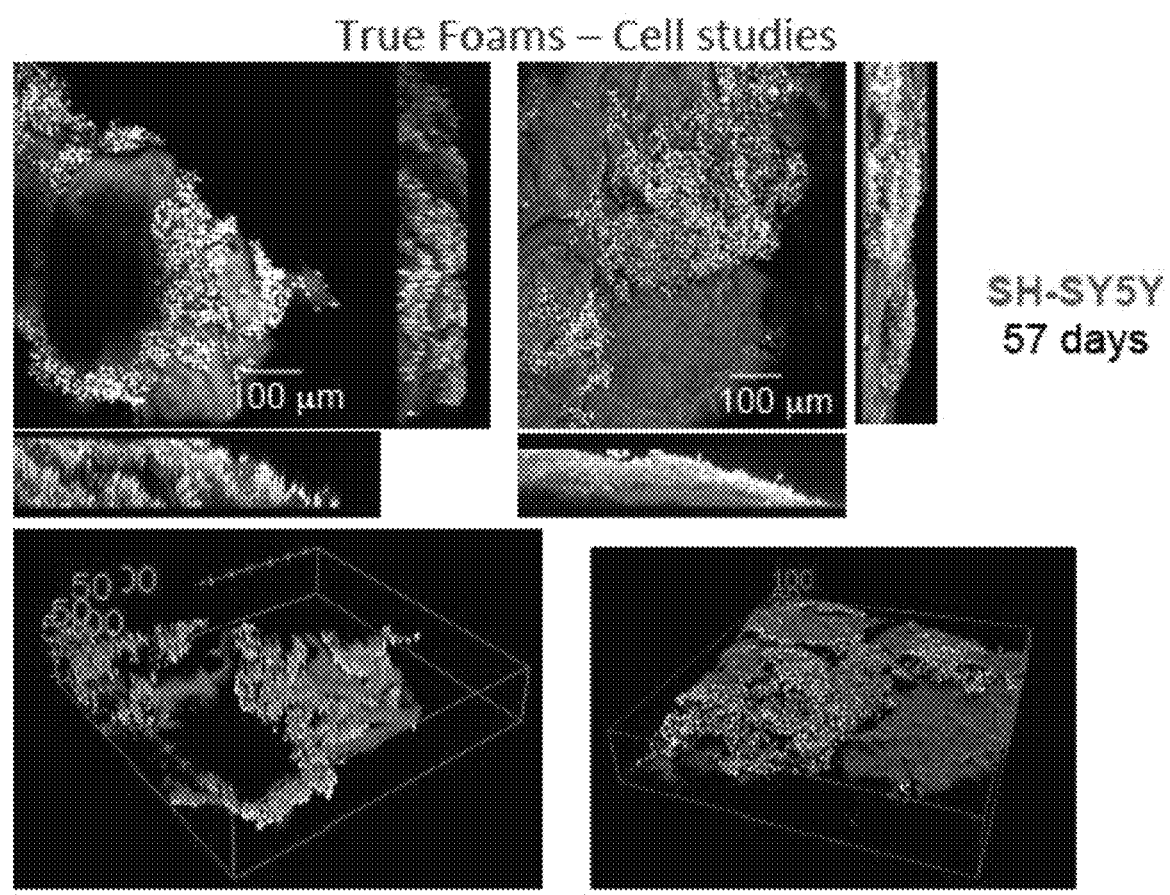
FIG. 28 shows, confocal microscopy images of 3D views from different angles, of SH-SY5Y cells grown on LCE foams for over 57 days.
Figure 30:
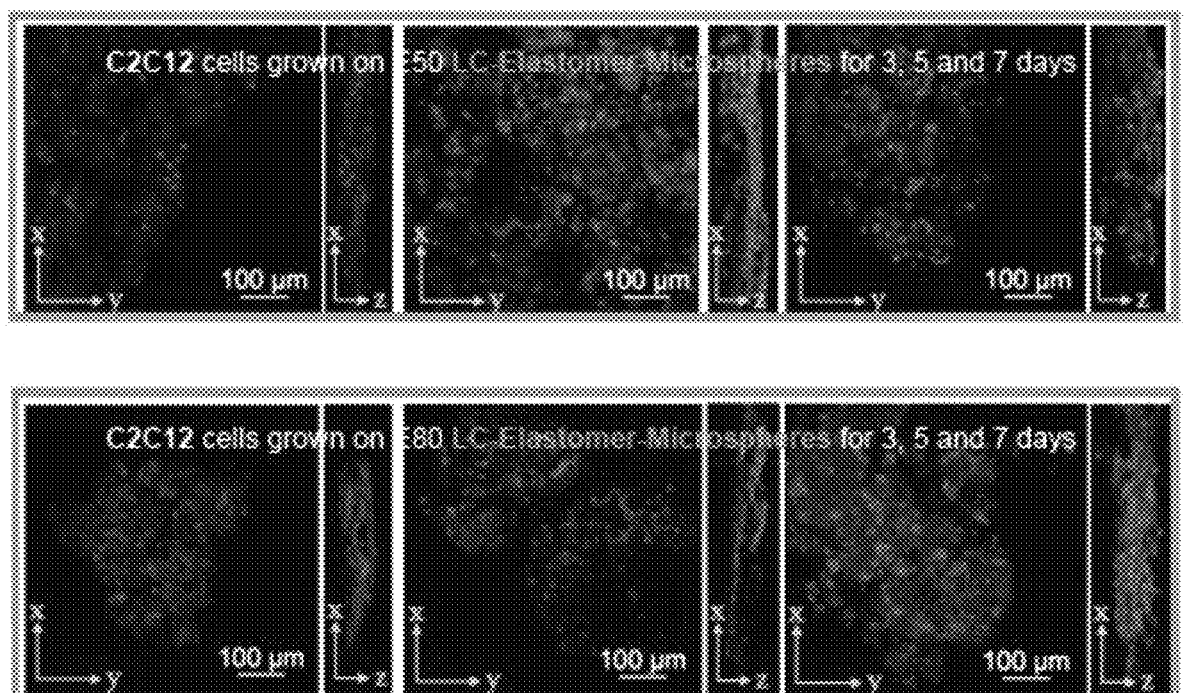
FIG. 30 shows confocal images of C2C12 cells grown on E50 and E80 globular LCEs for 3, 5, and 7 days comparing the amount of cells growing between the two globular morphologies. Globular elastomers were dyed with Rhodamine (red) and cell nuclei with DAPI (blue) for better contrast and show that cells do proliferate within the LCE.
Figure 31:
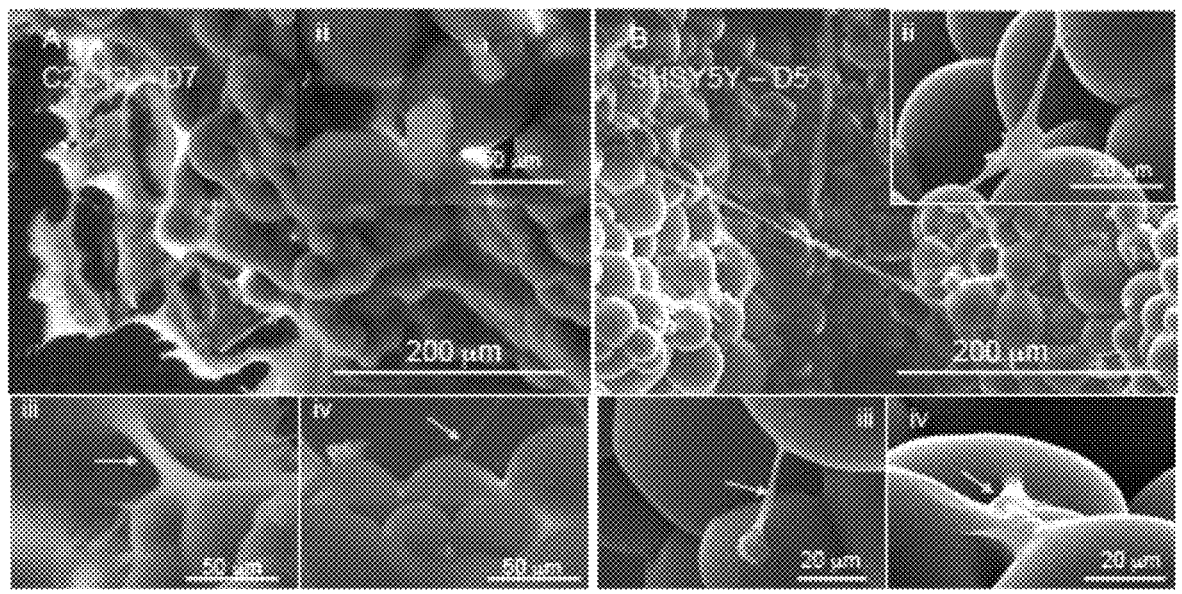
FIG. 31 shows SEMs of C2C12 and SHSY5Y cells growing within the globular LCEs, fibers can be seen attaching to the matrix for expansion and proliferation.
Figure 32:
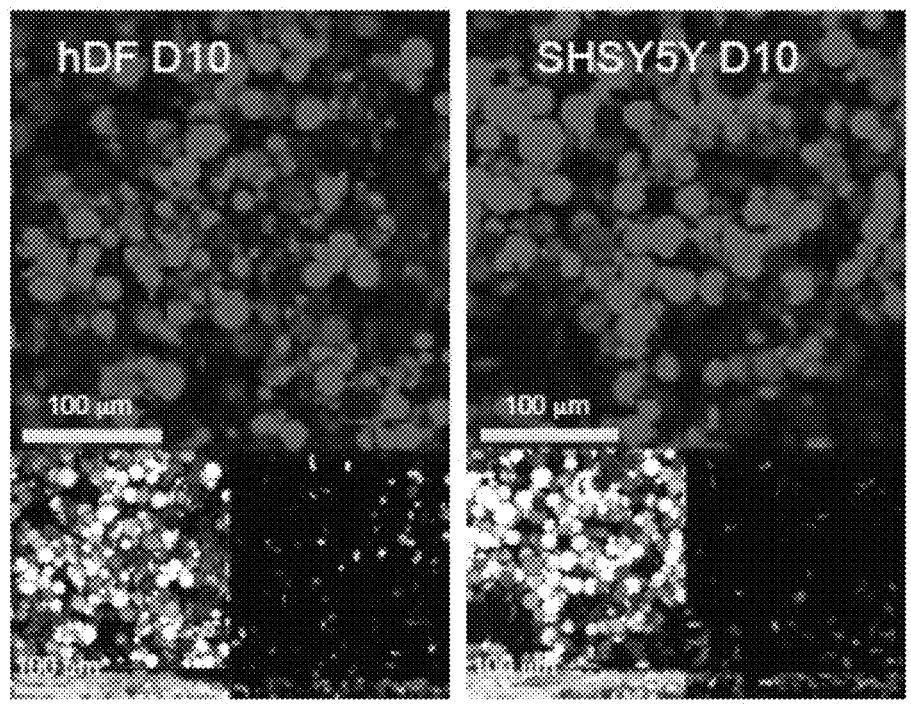
FIG. 32 shows another cell line human primary fibroblast (hDF) and compared to SHSY5Y (neuroblastomas) at Day 10 (D10). This slide together with FIG. 31 show that several types of cells can be grown also on nematic LCEs. Globular elastomers were dyed with Rhodamine (red) and cell nuclei with DAPI (blue) for better contrast and show that cells do proliferate within the LCE.
Figure 33:
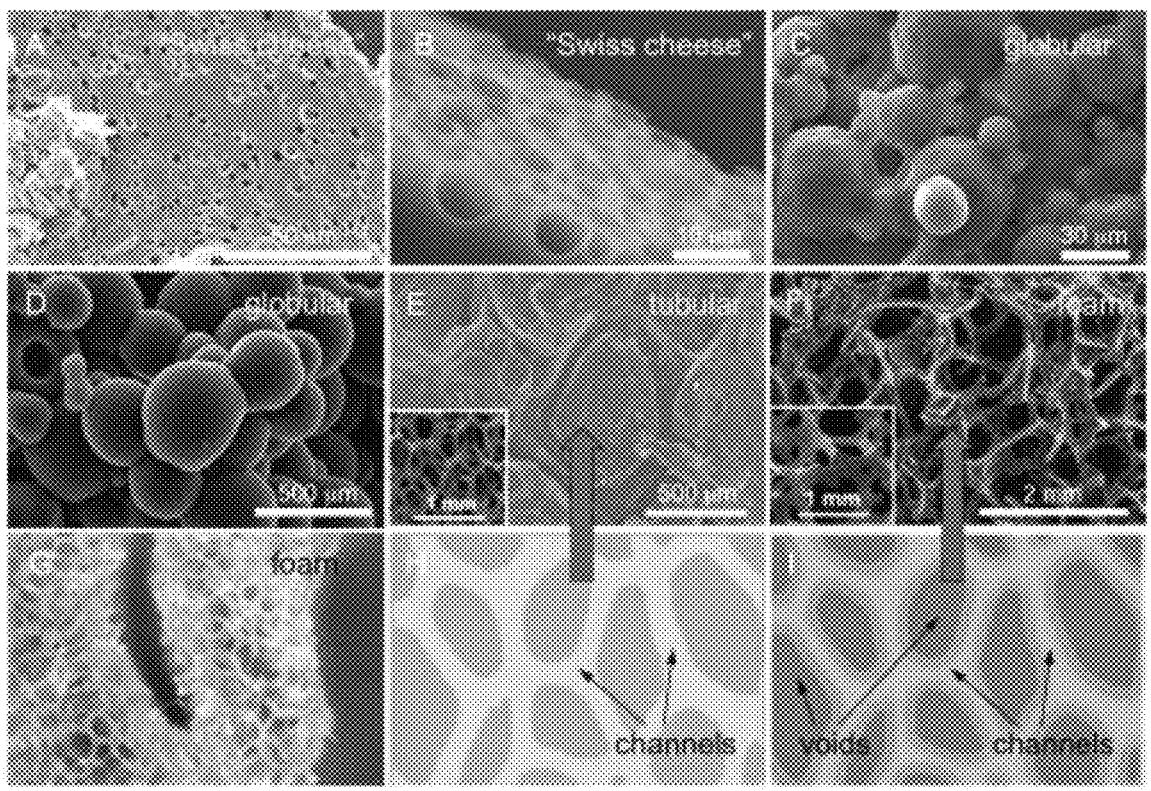
FIG. 33 shows all LCE morphologies prepared so far: A & B Swiss cheese like morphologies, C & D globular morphologies, E & H tubular or channel like morphology, F, G & I Foam LCE morphology.
Figure 34:
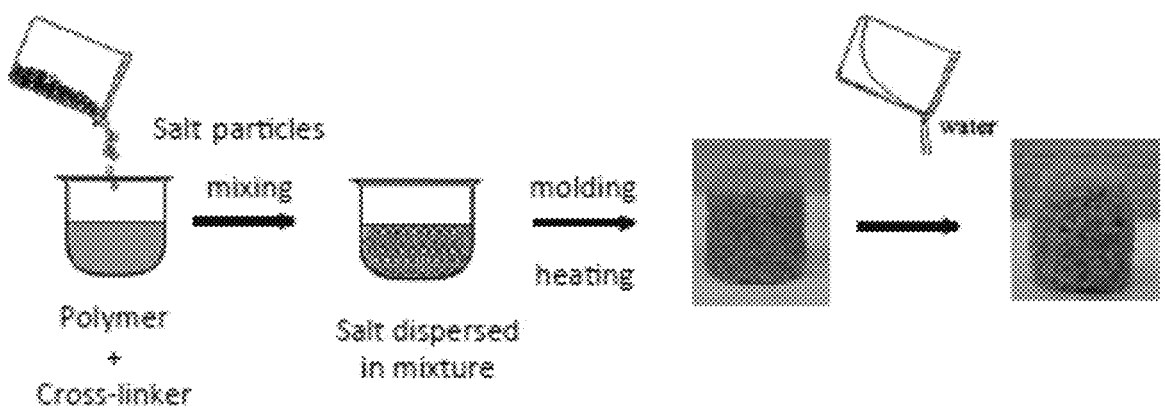
FIG. 34 shows, schematic of salt leaching new LCE foam preparation.
Figure 35:
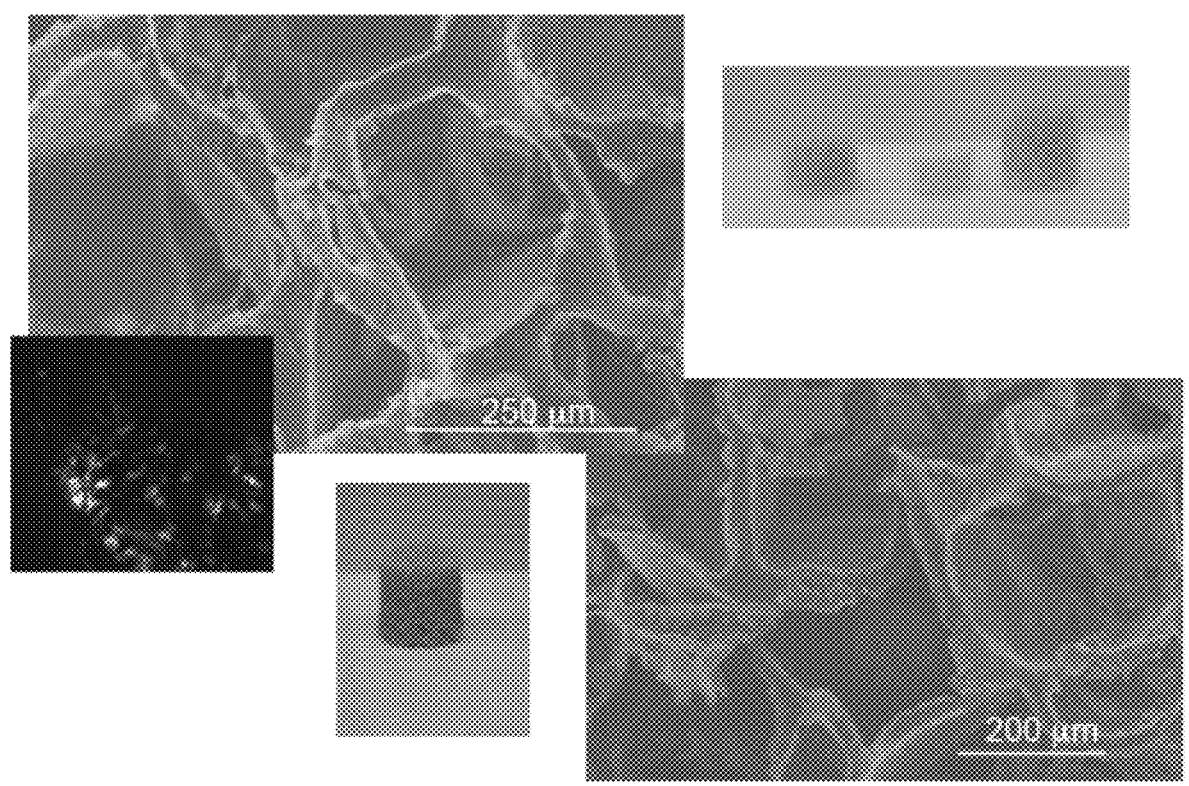
FIG. 35 shows SEM and optical images of salt-leaching LCE foam using salt (NaCl) particles. Far bottom left inset shows a polarized optical microscopy (POM) demonstrating that salt-leaching LCE foam is birefringent.
Figure 36:
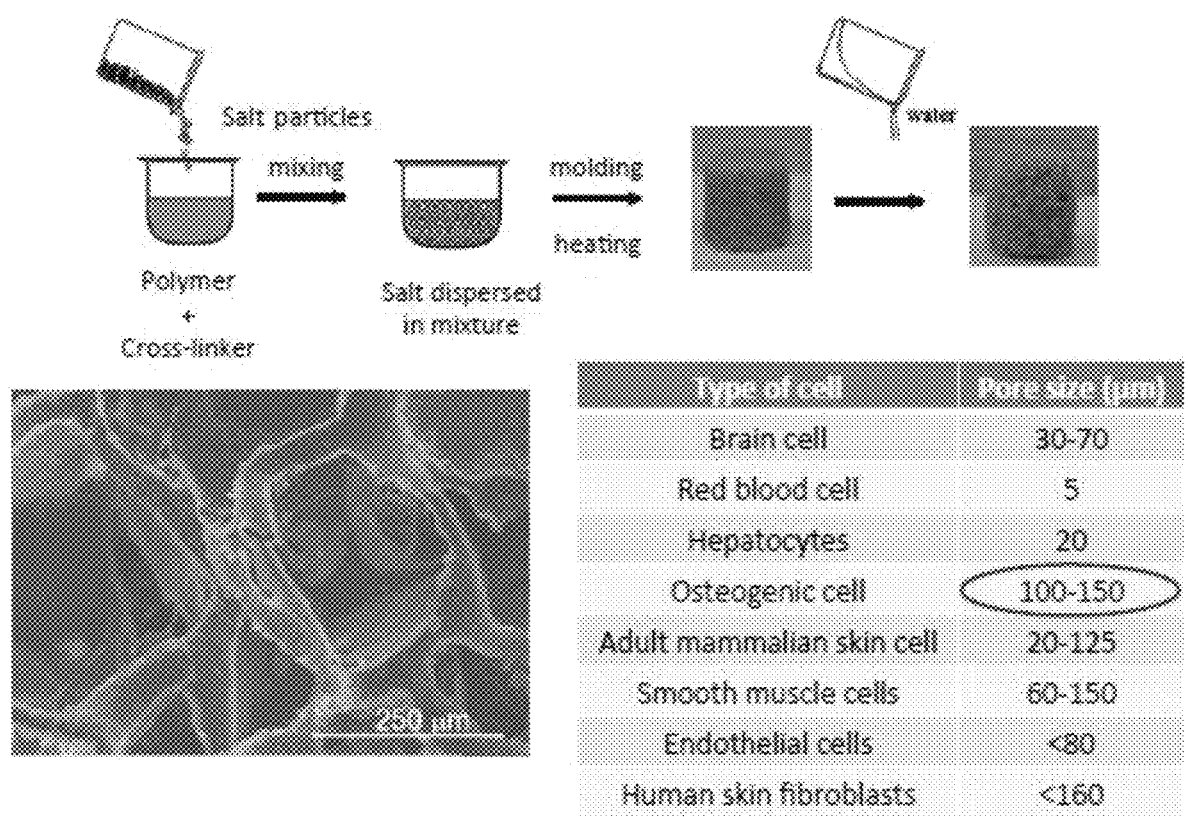
FIG. 36 shows SEM image of salt-leaching LCE foam with an average pore size of 250 um, that can be use for osteogenic cells.
Figure 37:
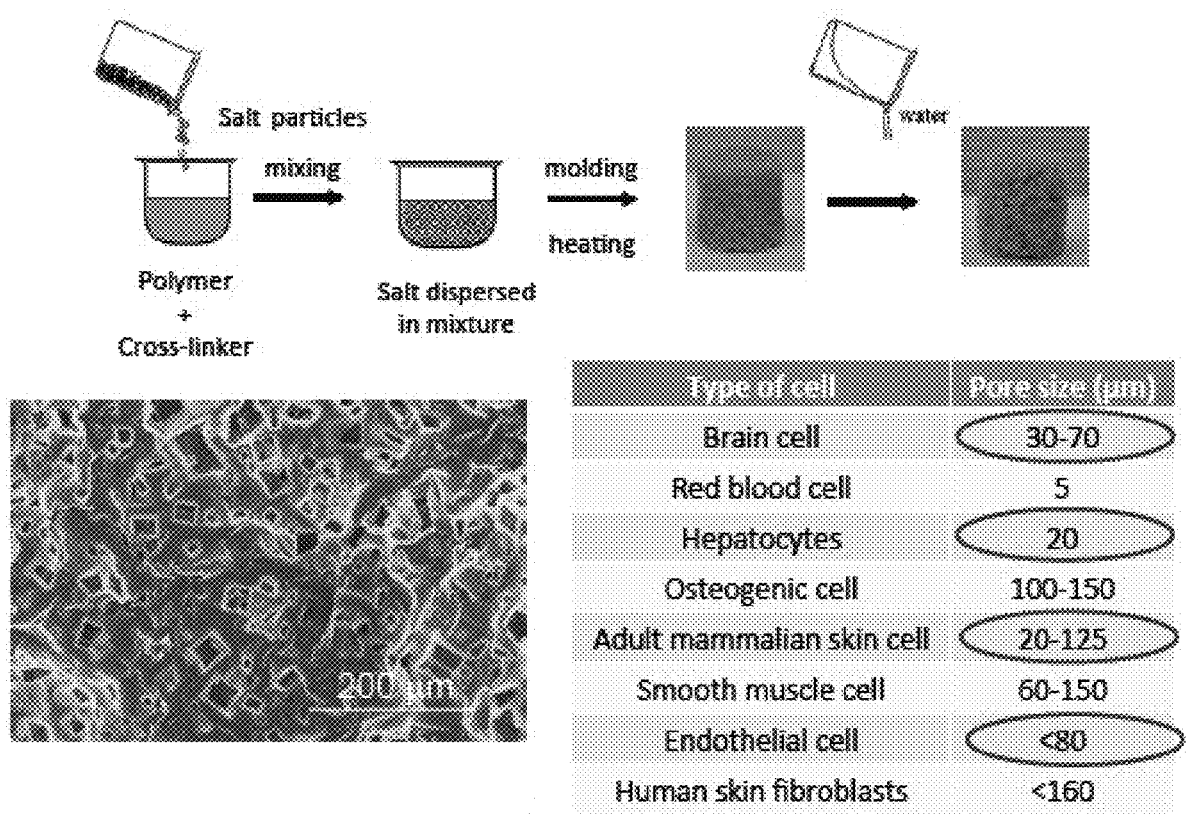
FIG. 37 shows SEM image of salt-leaching LCE foam, prepare with an engineered salt crystal, with an average pore size of 50 um, that can be use for brain, skin and endothelial cells among others.
Figure 38:
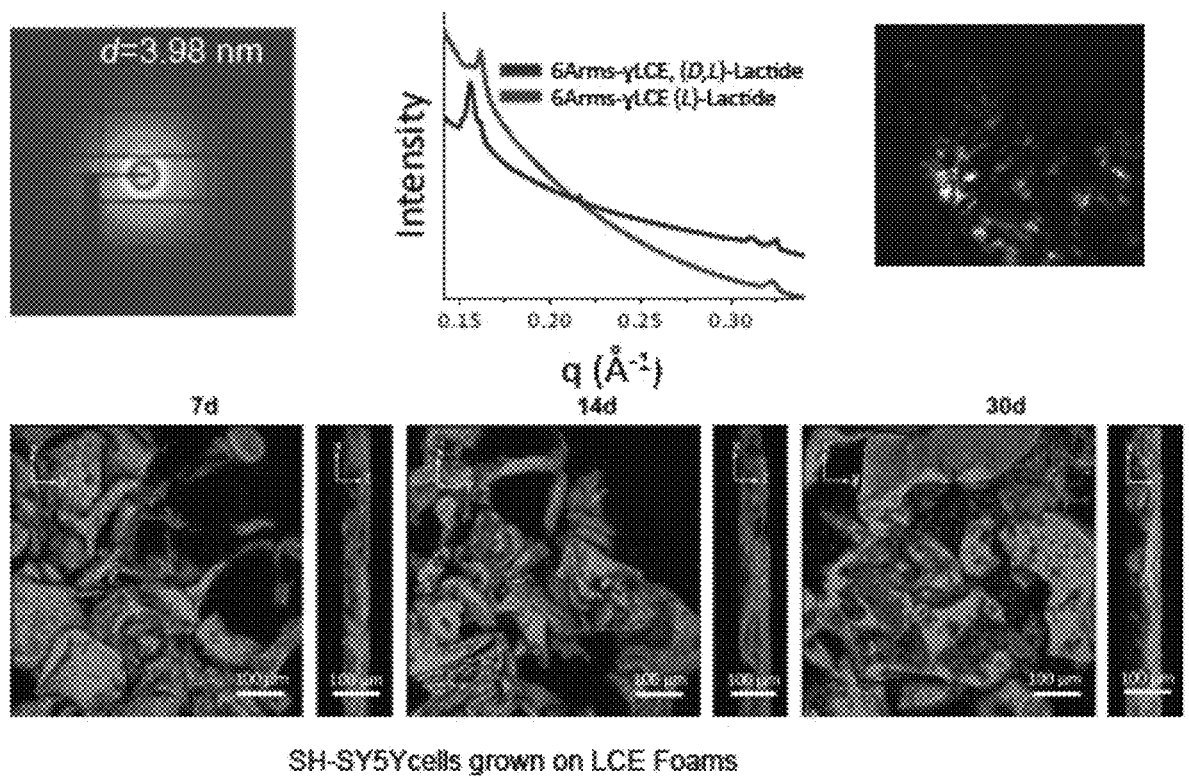
FIG. 38 shows: top left and top middle small angle x-ray diffraction (SAXD) data showing that salt-leaching LCE foam shows a SmA phase; top right POM image demonstrating birefringence of the LCE; bottom images are confocal images of SH-SY5Y cells growing within salt-leaching LCE foam on 7, 14 and 30 days demonstrating cell proliferation.
Figure 39:
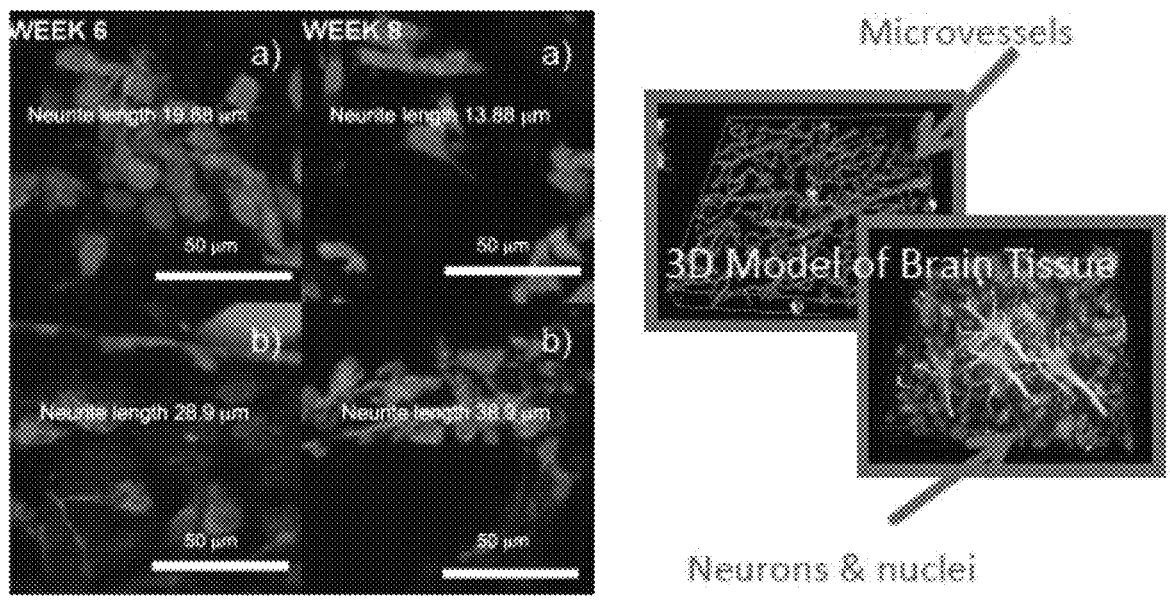
FIG. 39 shows left image is a composite of confocal images of SH-SY5Y cells growing on petri dishes (a) and LCE foams (b); comparing the neurite length petri dish vs LCE. Cells grown on LCE have in average longer neuritis than those grown on petri dishes after being stimulated with retinoic acid. Right images show a composite image of a mouse brain showing microvessels and neurons & nuclei among other cells. Our objective is to 3D print microvessels using our LCEs to later grow brain cells on top of them to be able to recreate a 3D Model of Brain Tissue.

Cells such as those set forth in Table 2 are readily available from various sources, such as American Type Culture Collection (ATCC, VA) or harvested from an animal of interest. Cells are grown in petri dishes as per conventional cell cultures (using prepared media for specific cell lines as per traditional methods) and once a suitable number for cells seeding in elastomers, cells are lifted from petri dishes (following traditional harvesting methods). A cell seeding solution (cells+relevant media), with a predetermined cell number is then seeded on the LCE foam. Cell seeding can be in several ways, such as on top of the elastomer, inside the elastomers, etc. Cells are then incubated at about 37° C. with 5% $CO_2$ (or specified for particular cell lines growing protocol), cell media is changed every two-three days (as pertinent for every cell line). Cells are allowed to proliferate for several weeks as predetermined by experimental protocols. A schematic of this process is set for in FIG. 14.

The schematic representation of the biodegradable, biocompatible liquid crystal elastomers of the present invention is set forth in Schemes 1 and 2 wherein various different cholesteric liquid crystal elastomers are crosslinked and form a matrix or scaffold containing the star block copolymers and crosslinking agents thereon.

Cell Cultures

Elastomers were seeded with mouse skeletal C2C12 myoblast cells or hDFs cells and cultured using standard sterile techniques. Growth medium for C2C12 contained 90% DMEM, supplemented with 10% FBS and 1% Pen-Strep. The elastomers were cut by using 8 mm diameter tissue punch and separated into four pieces with equal size. Prior to cell seeding, the elastomers were washed with 70% ethanol, UV irradiated for 10 min, and then washed by 70% ethanol again, rinsed twice with sterile water and PBS. Elastomers were pinned onto a 2% agarose with DMEM substrate to prevent cell adhesion to the petri dish culture surface in 24-well culture plates. Approximately $1.5 \times 10^4$ C2C12 cells (passages 8-12) suspended in growth 100 mL media were seeded onto each of the elastomers. The elastomers along with the cells were incubated at 37° C. with 5% $CO_2$, in a humidified chamber, for about 2 h to promote cell adhesion followed by addition of 0.5 mL growth media. Media was changed every other day after washing by 0.5 mL PBS. After 3, 5, 8, and 15 d, cells were fixed with 4% paraformaldehyde in PBS for 15 min, rinsed twice with PBS for 5 min. The fixed samples were stained with 0.1% DAPI with PBS for 10 min and rinsed twice with PBS for 5 min for fluorescence confocal microscopy analysis. Several images from the fluorescence confocal microscopy were sequentially taken and stacked into a 3D composite image using ImageJ. Image stacks were sequentially acquired using a fluorescence confocal microscope and spanned the sample thickness. 3D composite images were generated from the data and data analyzed using ImageJ Similar protocols were followed for the hDF cultures.

Cell Proliferation and Cytotoxicity Assays

Viability and proliferation of C2C12 skeletal myoblasts of the elastomer scaffolding were assessed in a complimentary fashion using the CyQuant cell proliferation assay. For the CyQuant cell proliferation assay the elastomers were cut into equivalent size square pieces of 5 mm×5 mm×1 mm and quart circle pieces of 8 mm diameter, respectively. The elastomer pieces were sterilized and seeded with $1.5 \times 10^4$ C2C12 or hDF cells, cultured for 15 d by the same method as described in the previous section (2.2.8). For the CyQuant cell proliferation assay, individual samples were removed at five time points (days 3, 5, and 8 for C2C12 as well as 6, 8, and 12 for hDF) and immediately frozen at −80° C. At the completion of the culture period, the frozen elastomer/cell constructs were thawed and the cellular content was assessed using the CyQuant reagent according to the manufacturers recommended instructions, and fluorescence intensity was measured with excitation at 480 nm and emission at 520 nm.

Cell Imaging and Orientation Analysis

Confocal data were analyzed using ImageJ including the alignment and orientation of hDF cell nuclei where raw data were converted to grayscale, and the hDF nuclei were traced by stylus pen on Power Point. Next, the images were binarized and skeletonized for directionally analysis on ImageJ. In this calculation, the order parameter becomes better with increasing number of elongated cells, but the parameter is not dependent on the width of the cells. Specifications of the Directionality (Fiji) plug-in were followed as described by the method developed by Jean-Yves Tinevez.

Synthesis

Liquid Crystal Elastomer Synthesis

Elastomers were prepared using a modified, previously reported method. For the synthesis of 3LCE-α, LC-modified polymer (3-SBC1-CLC), ε-caprolactone (ε-CL), and cross-linker 2,2-bis(1-caprolactone-4-yl) propane (BCP) at a ratio of 3:1:1 were used. In a clean dried flask 3-SBC1-CLC (10%) (3 g), ε-CL (0.99 g, 8.7 mmol), BCP (0.99 g, 3.68 mmol), and 3 mL of dichloromethane were added, vortexed, and then heated in oven at 140° C. until the BCP was dissolved. Then, tin(II) 2-ethylhexanoate (90 μL, 0.28 mmol) as catalyst was added and contents were again mixed using vortex to obtain a homogeneous solution. Thus obtained mixture was poured over silanized glass substrates and kept at 140° C. for 24 h in a vacuum oven for cross-linking. The resulting elastomer was then removed and was washed with 70% ethanol solution and dried at 45° C.

All other elastomer films (3LCE-γ, 4LCE-α, 4LCE-γ, 6LCE-α, and 6LCE-γ) were prepared following the exact same procedure, but replacing glycerol for pentaerythritol and dipentaerythritol to prepare the 4- and 6-arm LCEs, respectively. For comparison the authors also synthesized unmodified elastomers (using only ε-CL, eliminating the use of LC-modified CL). These are henceforth referred to as 3E (three-unmodified elastomer), 4E (four-unmodified elastomer) and 6E (six-unmodified elastomer). Table 1 shows a listing of all elastomers investigated in this invention.

Results and Discussions

Synthesis and Chemical Characterization of Polymers and LCEs

The cultured pathway pursued for the LC modified polymers is shown in Scheme 1. In a random ring opening polymerization ε-caprolactone (ε-CL), α-bromo-ε-caprolactone central node were polymerized using tin(II) 2-ethylhexanoate as a catalyst to obtain 3-arm star block-copolymer (3-SBCα-Br). Then, in subsequent steps the bromo (α-Br) group was substituted with azide (—N3) to obtain 3-SBCα-N3. Displacement of the bromo (α-Br) by the azide (—N3) was confirmed by the appearance of the 2099 cm-1 band in the ATR FT-IR spectrum and higher chemical shifts of specific protons in the 1H NMR spectra. The chosen LC pendant, cholesterylhexynoate, was covalently attached to the star blockcopolymer using alkyne-azide Huisgen's cycloadditon reaction ("click" reaction) obtaining 3SBCα-CLC. The disappearance of the 2100 cm-1 band and the appearance of a new band at 3263 cm-1 in the FT-IR spectra confirmed success of reaction. The formation of the triazole ring was also confirmed by the presence of a singlet observed at 7.30 ppm in 1H NMR spectra. We also studied effect of placement of halogen group either at alpha (α-Br) or gamma (γ-Cl) position to the carbonyl on the functionalized ε-CL (3SBCα-CLC or 3SBCγ-CLC). Then, we studied the effect of replacing the central node in the copolymers with 4-arm (4SBC-α/γ) and 6-arm (6SBC-α/γ) central cores. All central nodes serve as both initiators and intrinsic cross-linkers. At each step, the modification of functional groups was carefully monitored using 1H NMR and FT-IR spectroscopy. 1H NMR, FT-IR, TGA, and DSC were used to characterize all star-block-copolymers before crosslinking (3-SBC-α/γ, 4-SBC-α/γ, and 6-SBC-α/γ, 3-SBC-α/γ, 4-SBC-α/γ, and 6-SBC-α/γ). Thereafter, all SBCs (3-SBC-αCLC, 3-SBC2-γCLC, 4-SBC1-αCLC, 4-SBC2-γCLC, 6-SBC1-αCLC, and 6-SBC2-γCLC) were cross-linked using BCP to obtained 3LCE-α, 3LCE-γ, 4LCE-α, 4LCE-γ, 6LCE-α, and 6LCE-γ, respectively. DSC data confirmed that all modified SBCs were semicrystalline in nature while LCEs were amorphous and exhibited glass transition temperatures well below physiological temperature. SEM images (FIG. 1) were taken to determine the surface and internal morphology of the obtained final LCEs of the α-series, γ-series as well as the unmodified elastomers (3E, 4E, and 6E). All α-LCEs show a porous "Swisscheese" type morphology (FIG. 1d,e), whereas the γ-LCEs display a more flaky-type morphology (FIG. 1g-i). The unmodified elastomers in contrast showed a much smoother surface as well as bulk when compared to the two LC-modified series (see FIG. 2a-c). The difference in porosity and overall morphology could be explained by the presence and steric demand of the pendant cholesterol groups. With the LC pendants in the sterically more demanding α-position to the ε-CL carbonyl groups, less elastic but more porous structures are expected considering thermal expansion and contraction during crosslinking. The absence of LC pendant units leads to smooth materials for the non-modified elastomers, and sterically more flexible LC pendants in the γ-position elastomers should lead to elastomers with lower porosity but higher elasticity. We will see later that the mechanical properties of the α- and γ-series corroborate this to some extent.

TABLE 3

| Elastomer | $q_{(hkl)}$ [Å$^{-1}$] | d [nm] |
|---|---|---|
| 3LCE-γ | $q_{(001)} = 0.155$ | 4.04 |
|  | $q_{(002)} = 0.31$ | 2.03 |
| 4LCE-γ | $q_{(001)} = 0.16$ | 3.94 |
|  | $q_{(002)} = 0.32$ | 1.98 |
| 6LCE-γ | $q_{(001)} = 0.153$ | 3.98 |
|  | $q_{(002)} = 0.316$ | 1.98 |

Figure 2:
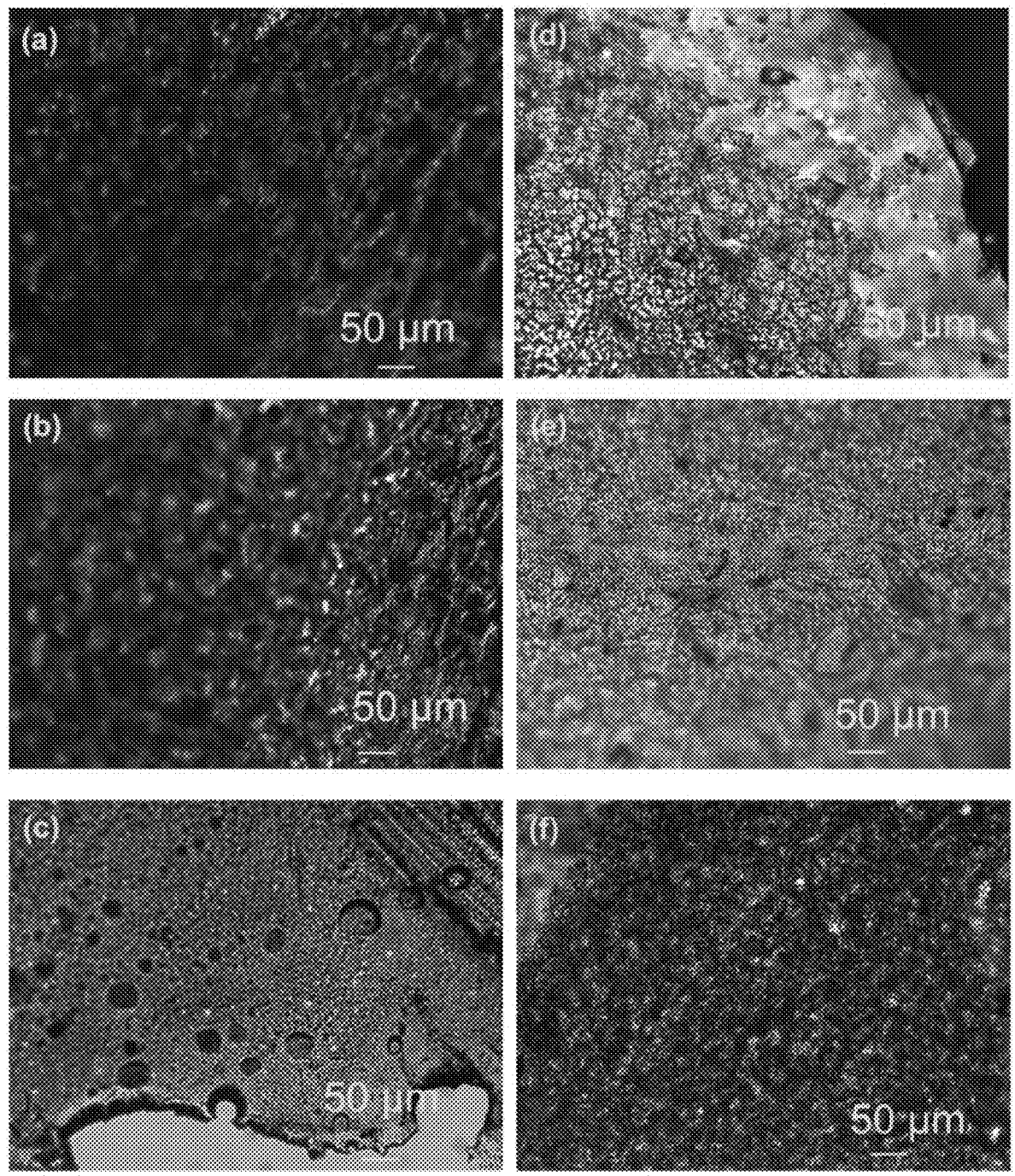
FIG. 2 shows POM images of LCEs between untreated glass slides on cooling from the isotropic liquid phase (90° crossed polarizers) of a) 3LCE-α (at 53.4° C.), b) 4LCE-α (at 75.0° C.), c) 6LCE-α (at 31.7° C.), d) 3LCE-γ (at 30.7° C.), e) 4LCE-γ (at 49.9° C.), and f) 6LCE-γ (at 41.5° C.)
Figure 3:
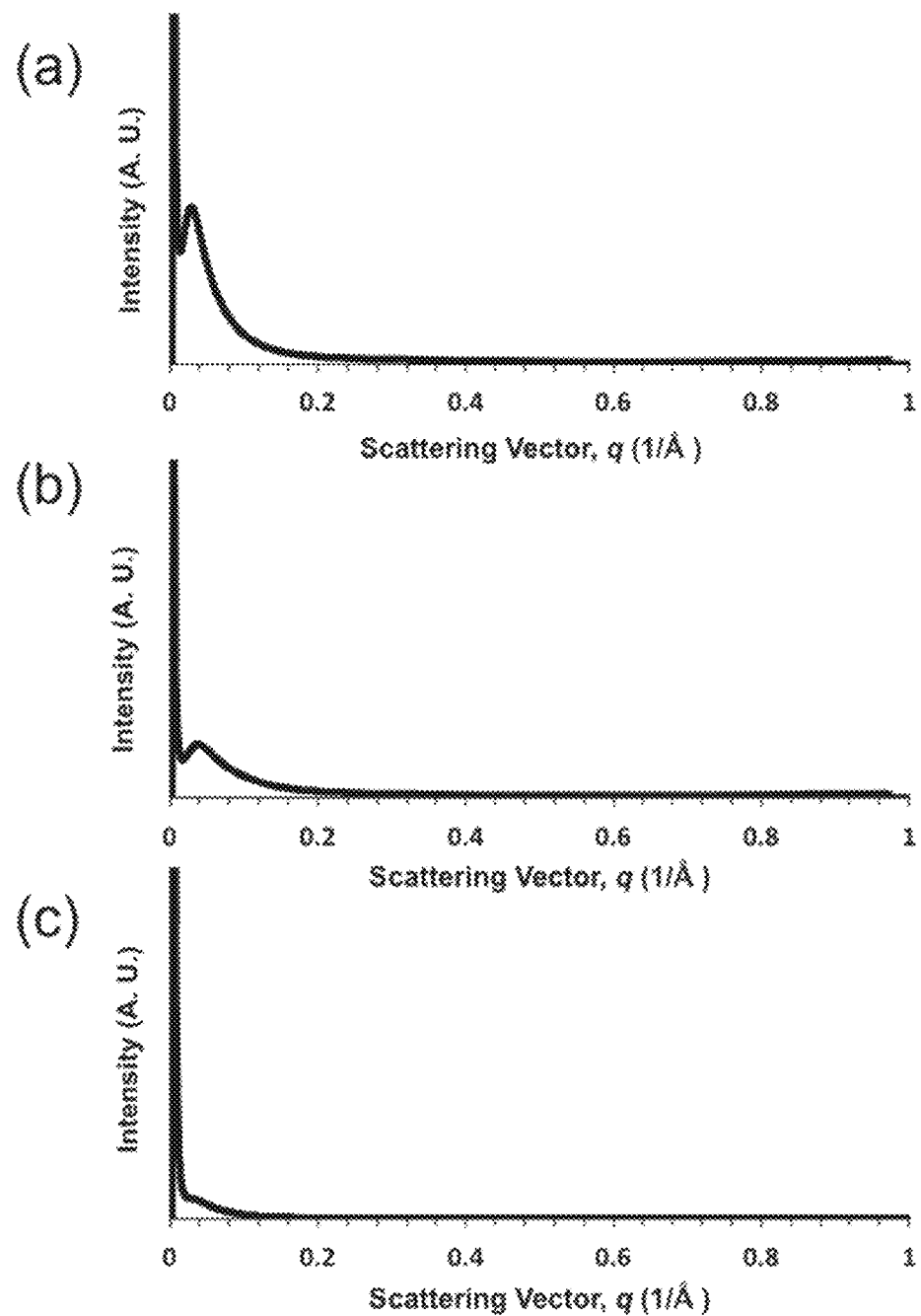
FIG. 3 shows an azimuthally averaged intensity data of the scattering vector (q in Å$^{-1}$) versus intensity of 2D SAXD pattern with corresponding X-ray diffraction pattern of a) 3E, b) 4E, and c) 6E.
Figure 4:
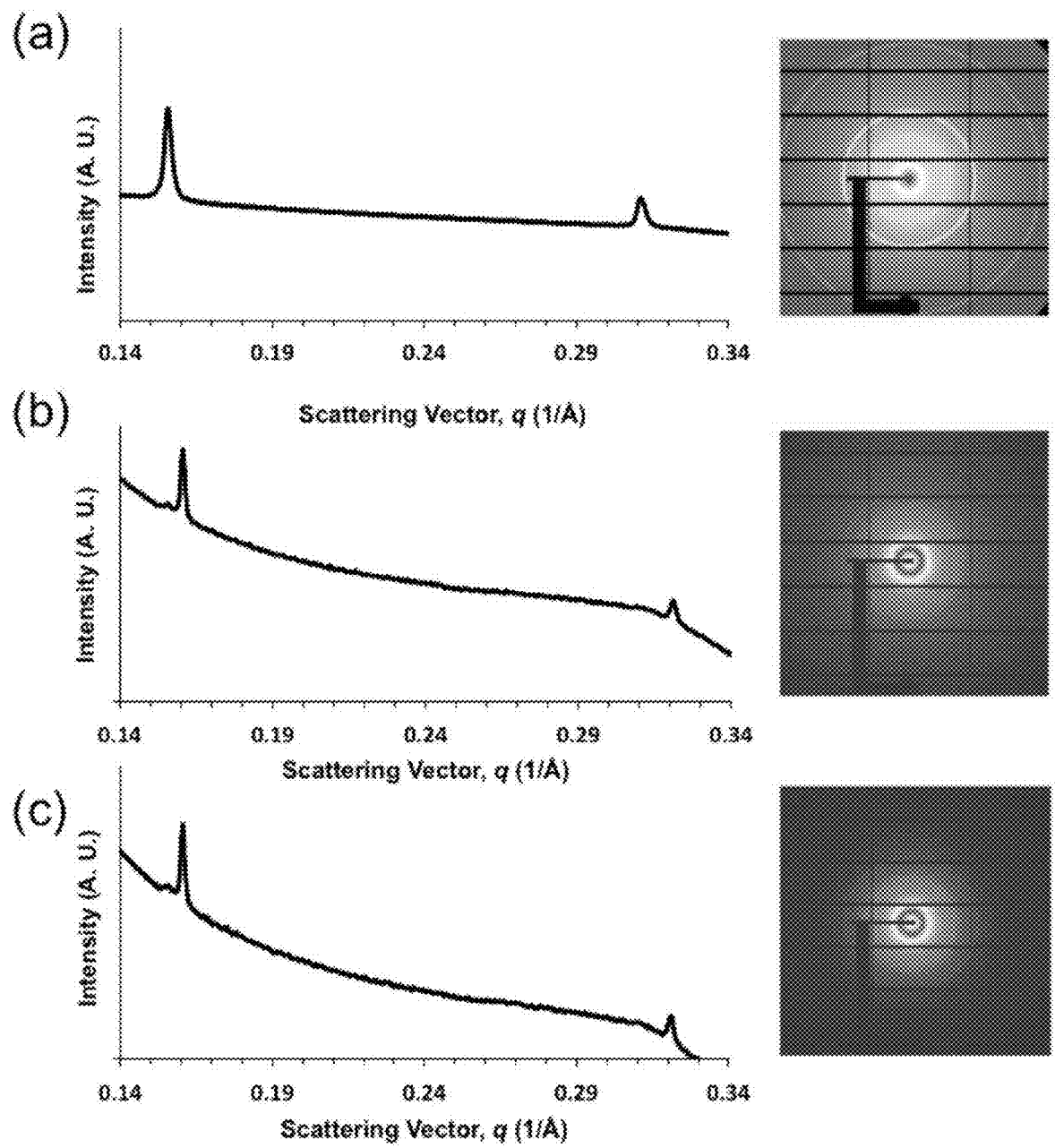
FIG. 4 shows an azimuthally averaged intensity data of the scattering vector (q in Å$^{-1}$) versus intensity of 2D SAXD pattern with corresponding X-ray diffraction pattern of a) 3LCE-γ, b) 4LCE-γ, and c) 6LCE-γ.

Measured scattering vectors (q in Å$^{-1}$) with respective Miller indices and calculated d spacing in nm Liquid Crystalline Properties and Morphological Characterization The liquid crystalline properties of the LCEs were characterized using POM and SAXD. All the LCEs films (α and γ) were observed under temperature-controlled POM between plain, untreated glass slides (FIG. 2). The textures were fairly nonspecific, and as frequently observed for LCEs, do not show characteristic textural patterns that would give any first insights into the possible LC phase formed. However, by gentle pressing, birefringent patterns (somewhat resembling the SEM morphological features) can clearly be seen in all images. The 2D SAXD patterns for the unmodified elastomers and the γ-LCEs are shown in FIGS. 3 and 4, respectively. Table 3 summarizes the X-ray diffraction data for the γ-LCEs. For the α-series, SAXD pattern for 3-LCE-α were reported earlier and provided clear evidence for the formation of a smectic-A phase with interdigitated cholesterol moieties. 4-LCE-α and 6-LCE-α were too weak and the films broke during stretching to prepare thin films for SAXD measurement. However, they show similar textural features in POM and do likely form the same LC phase as all other LCEs reported here. The SAXD patterns for the γ-series each show two sharp scattering peaks in the mid-angle region (q1≈0.15-0.16 Å-1 and q2=0.32 Å-1) indicating ordered layer (i.e., smectic) structures (FIG. 4). In addition, the q-values are rather similar to data previously reported by our group for the 3-arm α- and γ-position LCE materials. In analogy, we assume that the values for 3-, 4-, and 6LCE-γ correspond to a nearly fully interdigitated smectic-A (SmA) phase type ordering. As shown in FIG. 4 the SAXD patterns for the three unmodified elastomers show no sharps peaks in the same q-range (i.e., no peak with a maximum above 0.05 Å-1), but broad scattering maxima at lower q-values (between 0.03 and 0.04 Å-1) hinting at the amorphous nature of these elastomers.

Thermal Characterization of LCEs

TGA of all unmodified, α- and γ-elastomer series have higher decomposition temperatures and are more stable that the more-volatile counterpart copolymers which follows the pattern that we previously reported. DSC data also corroborated our previous report confirming all glass transition temperatures (Tg) values significantly below physiological temperatures. Tgs values increased after crosslinking and all elastomers appeared amorphous showing no presence of endothermic melting peaks.

Mechanical Behavior of LCEs

Figure 5:
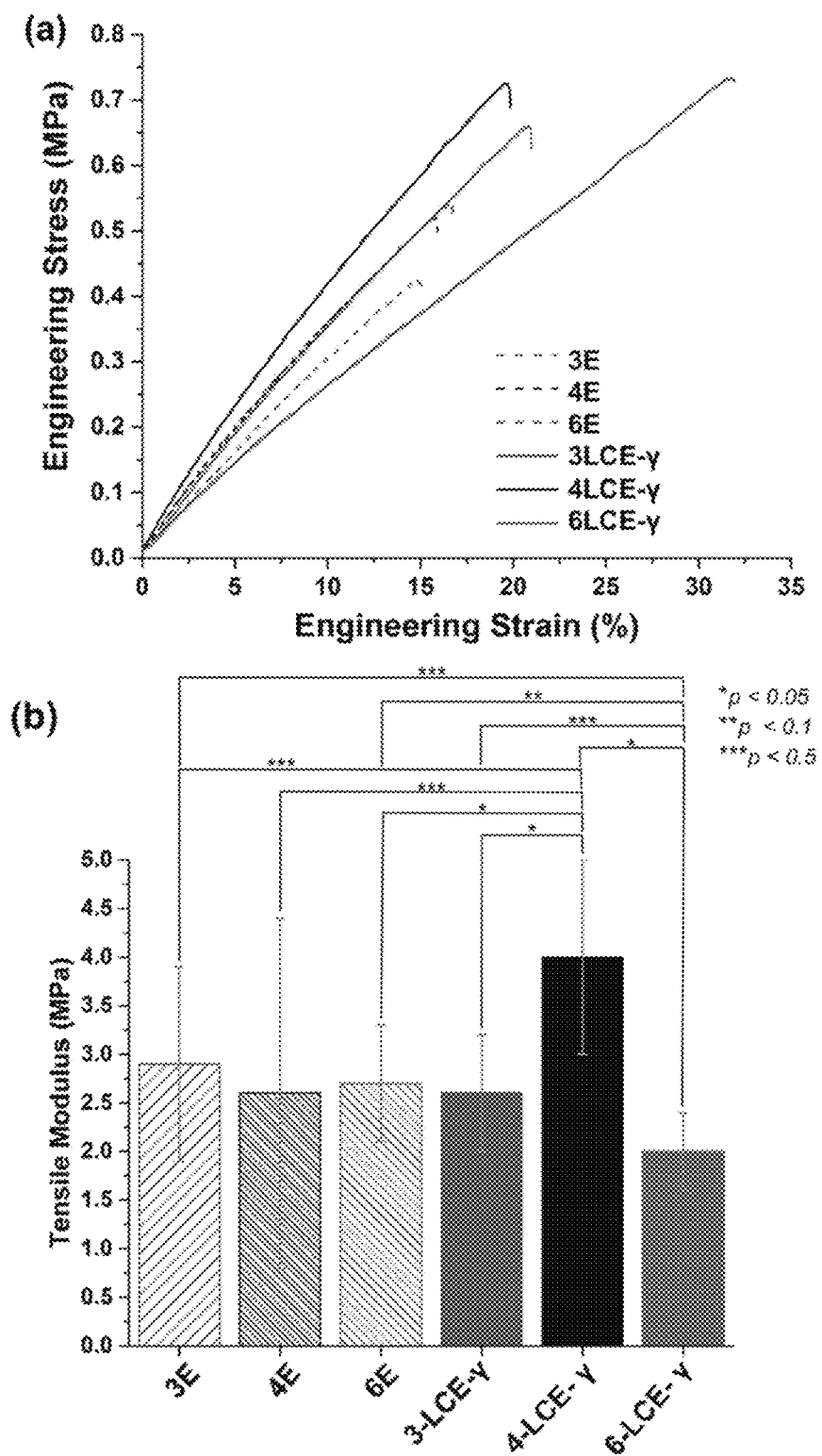
FIG. 5 shows a) stress-strain curve (representative curves determined by closest value to the average $\sigma_M$ and $\varepsilon_B$) and b) elastic modulus data for γ-series LCEs and unmodified elastomers (3E, 4E, and 6E)

Uniaxial tensile testing was used to analyze the mechanical properties of the unmodified elastomers (E3, E4, and E6) and liquid crystal elastomers at the γ-position (3LCE-γ, 4LCE-γ, and 6LCE-γ). Based on the representative stress-strain curves (FIG. 5a) and calculated E values (FIG. 5b), no clear correlations or trends were observed between the number of arms or the presence of LC pendant groups in the LCE films. Mechanical evaluation of the 4LCE-γ shows that modulus can potentially be affected due to the number of arms, which may correlate well with observations made during the cell culture experiments. Previous theoretical and experimental studies have shown that tetra-arm polymer hydrogel systems have extremely high homogeneous packing and suppressed heterogeneity. We previously reported 3LCE-α and 3LCE-γ; however, due to the new film preparation method the obtained 4LCE-α and 6LCE-α were weaker and broke more easily than their γ-counterparts (similar mechanical weakness was also observed during SAXD measurements). It is important to note that the moduli of all elastomers examined here are lower (=2.0-4.0 MPa) than those of the tissues formed by the cells investigated (30 MPa for skin and 350 MPa for muscle) as well as lower than for other widely used biodegradable polymers, likely due to the low molecular weight and nonlinear star-block structure. These preliminary mechanical results show a promising future for the use of LCEs in designing biomaterials for extracellular matrices. Cells are not only able to expand and proliferate, but tend to align on and within such LCE scaffolds without the use of any external stimuli.

Cell Studies

Figure 6:
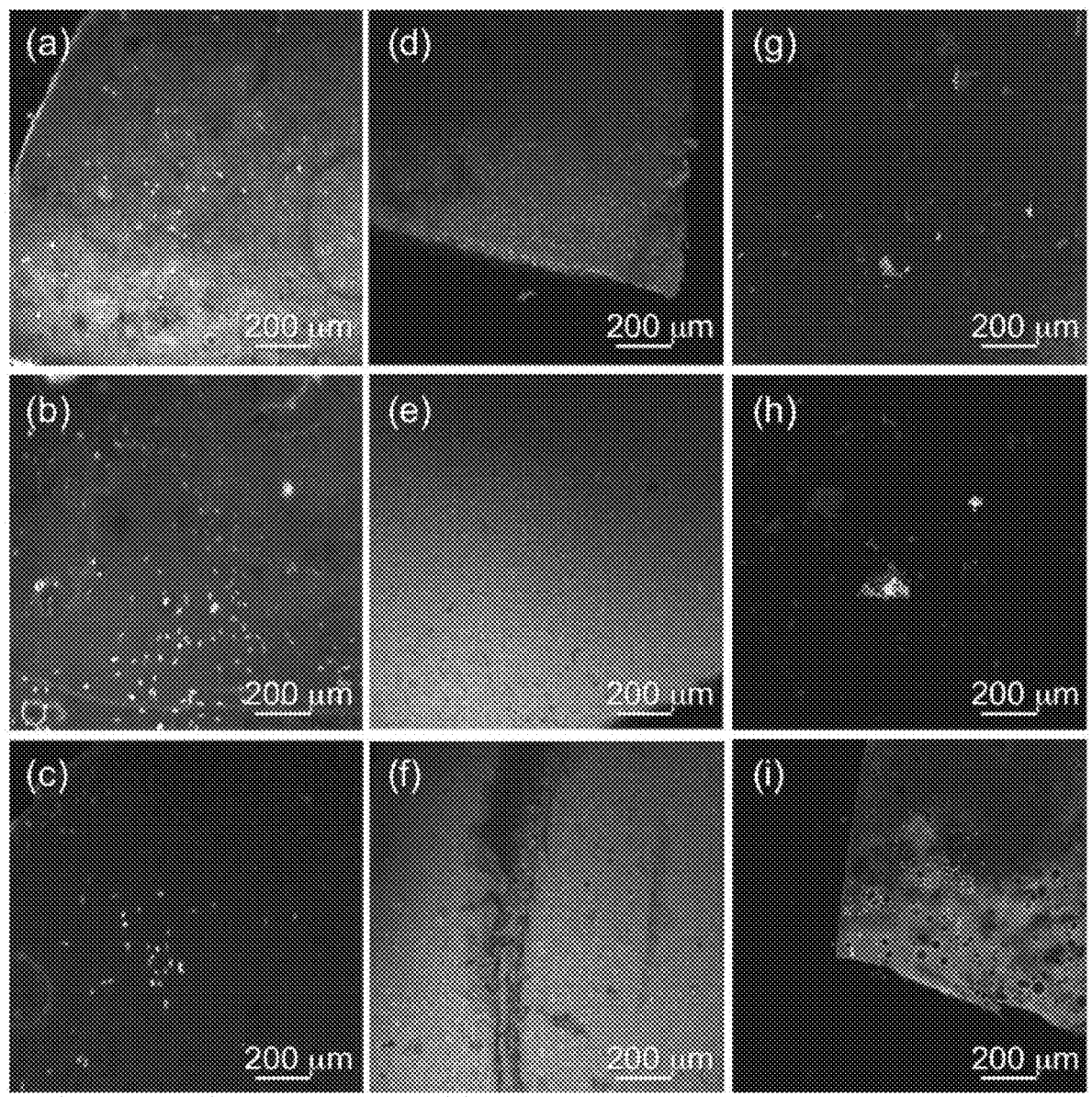
FIG. 6 shows C2C12 skeletal myoblasts grown on the elastomers films for 8 d and nuclei stained with DAPI and data acquired using confocal microscopy a) 3E, b) 4E, c) 6E, d) 3LCE-α, e) 4LCE-α, f) 6LCE-α, g) 3LCE-γ, h) 4LCE-γ, and i) 6LCE-γ.
Figure 7:
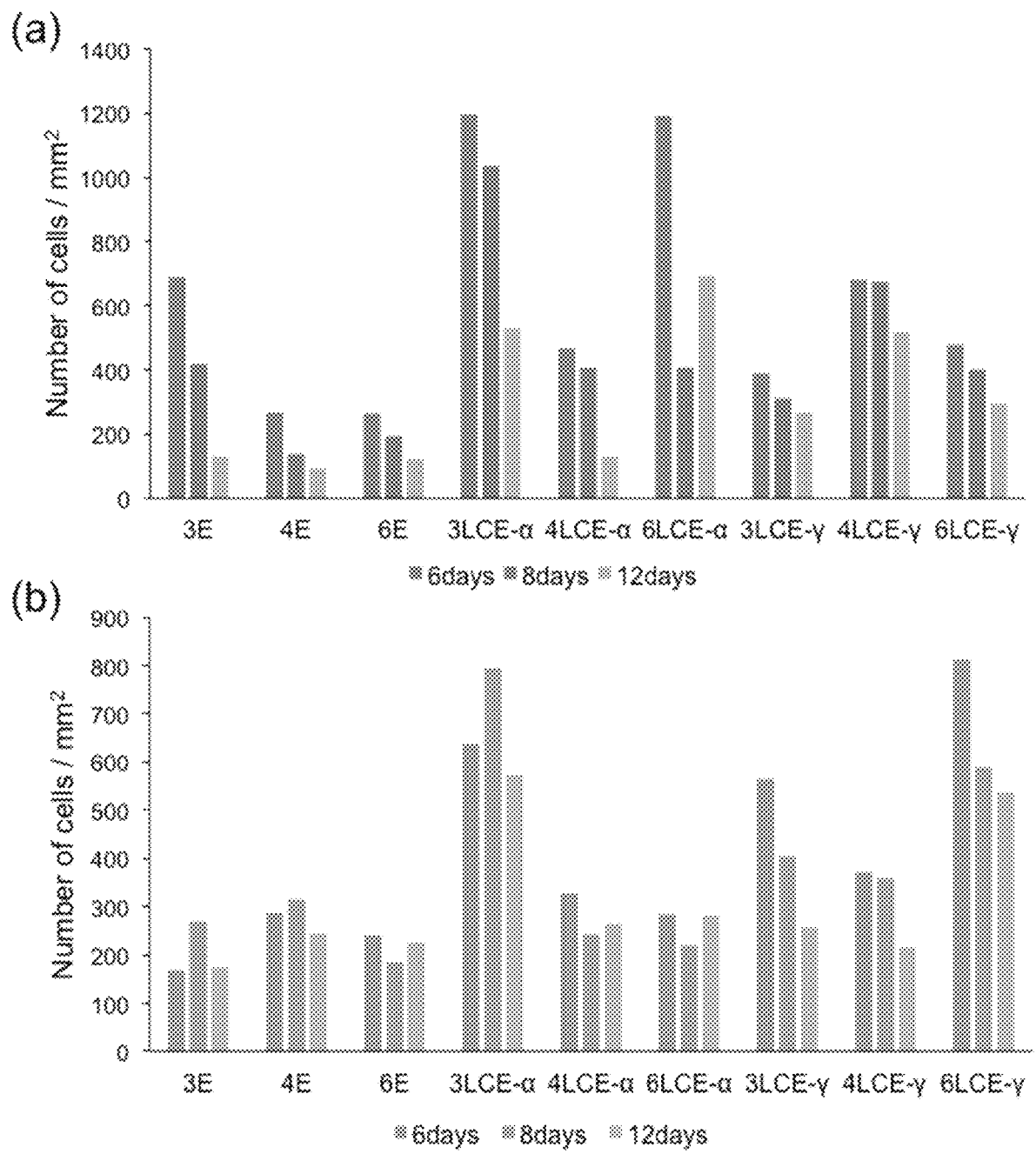
FIG. 7 Cell viability assay using CyQuant for a) 1.5×10$^4$ C2C12 cells growing on (10 mm2, rectangle 5 mm by 2 mm): unmodified, α-series LCEs and γ-series LCEs and b) 1.5×10$^4$ hDF cells growing on (10 mm2, rectangle 5 mm by 2 mm): unmodified, α-series LCEs and γ-series LCEs.
Figure 8:
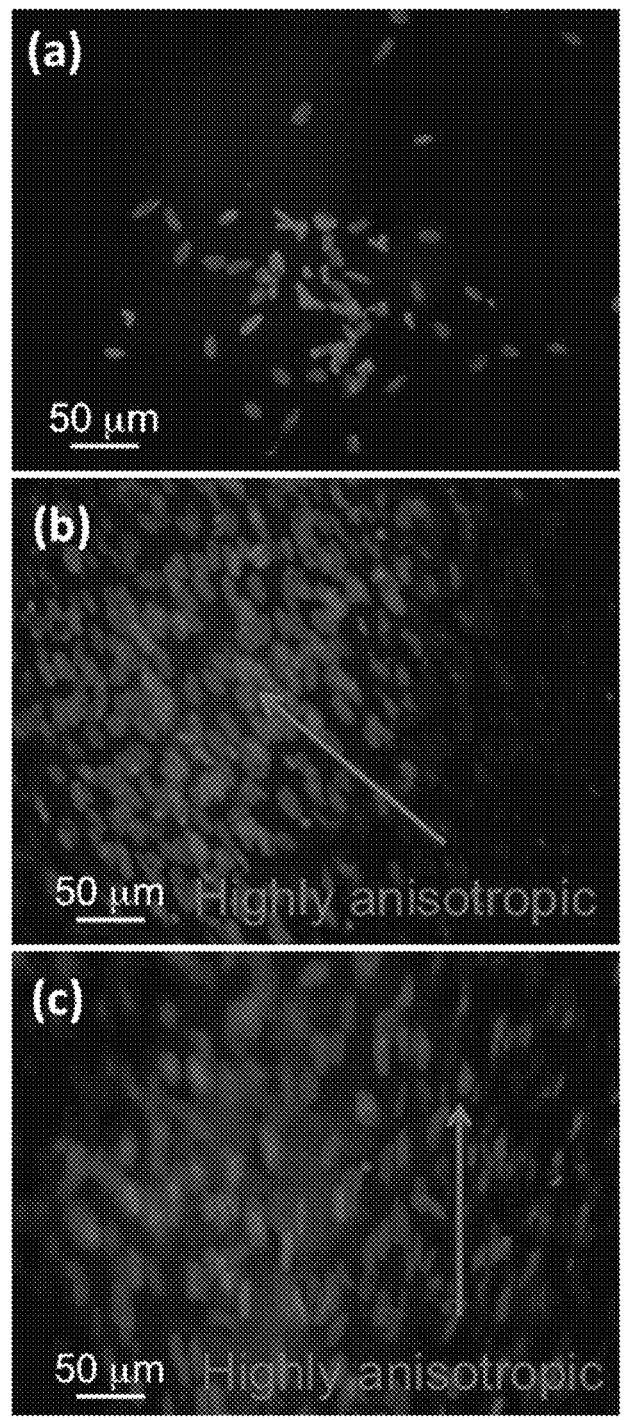
FIG. 8 is a Primary human dermal fibroblast (hDF) cultures grown for 5 d on a) 3LCE-α, b) 4LCE-α, and c) 6LCE-α elastomer films.

To determine the viability of cells on and within the LCEs we first tested murine myoblasts C2C12 cells on the α- and γ-series LCEs and for comparison also on the unmodified elastomers 3E to 6E. FIG. 6 shows the fluorescence confocal images of cells cultured for 8 d on 3LCE-α, 4LCE-α, and 6LCE-α as well as on the unmodified elastomers. From these images, it can be seen that the α-series LCEs provide a better platform for the attachment and proliferation of C2C12 and hDF cells than the unmodified elastomers (indicated by a much higher number of much more evenly and closely spaced cell nuclei). This is further confirmed by the CyQuant cell viability assay. FIG. 7a,b shows the CyQuant cell viability assays for both C2C12 and hDF growing on unmodified as well as the α- and γ-series LCEs. Both α- and γ-LCEs in general outperform their respective unmodified elastomer counterparts with the same central node by showing an overall increase in cell proliferation. It was observed that among all LCE-αs 3-arm LCEα showed a higher proliferation of both C2C12s and hDF cells. However, among the LCE-γ's, the 4LCE-γ showed the best proliferation rate for C2C12 cells while the 6LCE-γ was optimal for hDF cell proliferation. Since different cell types prefer an elasticity regime of the supporting scaffold matching native tissue, it was assumed that the elastic properties, depending on the type and density of cross-linking imparted by the various central nodes, are responsible for this observation (especially considering that most other parameters are constant among each series). This highlights the fact that modified LCE's for cellular growth should be carefully selected based on the intended cell types to be grown to provide the most optimal proliferation rates. We also performed confocal microscopy studies of the α-series LCEs with primary hDF cells. FIG. 8 shows the confocal fluorescence microscopy images of hDF cells cultured on the α-series LCEs for 5 d. Cell attachment, and by virtue of the cell number seeded on day 1, also proliferation, is seen on all three LCE scaffolds (3LCE-α, 4LCE-α, and 6LCE-α). Remarkable, however, is the fact that the images show anisotropic cell growth, especially for 4LCE-α and 6LCE-α. No external stimulus (i.e., stretching) was applied to the elastomer samples, indicating that directional cell growth might be a response to the lamellar (layer-like) molecular structure of the LC components (pendants) embedded within the scaffold network. However, additional and more detailed experiments on cell proliferation in the presence and absence of external stresses are required to gain further insight into this behavior.

Cell Alignment Studies

Figure 9:
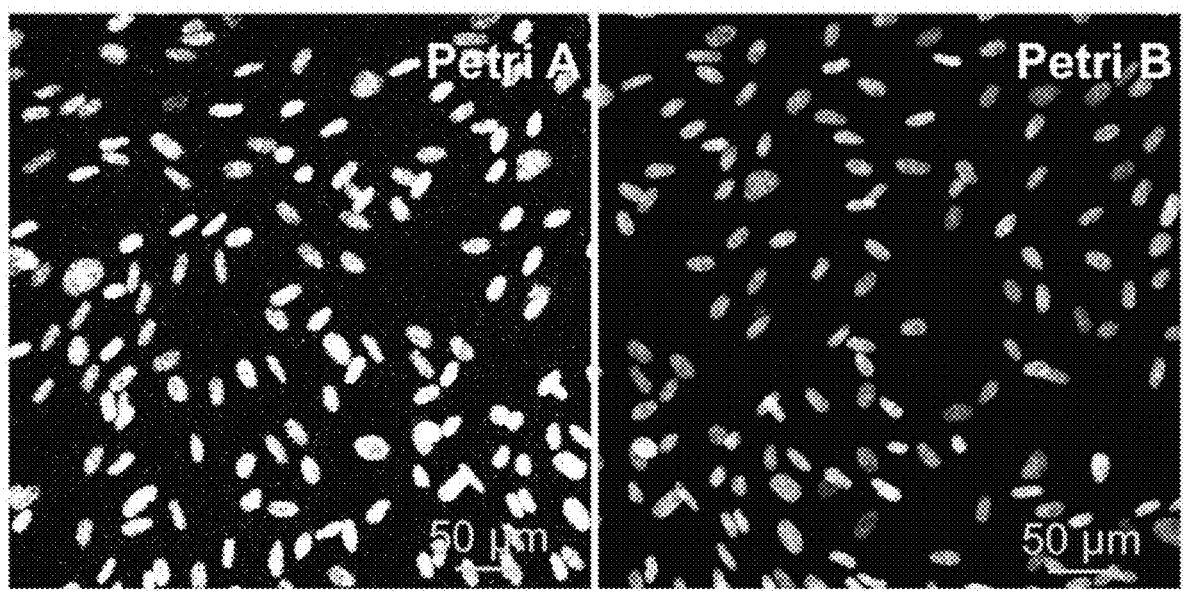
FIG. 9 shows Directionality analysis of primary human dermal fibroblast (hDF) cells grown on petri dishes.
Figure 10:
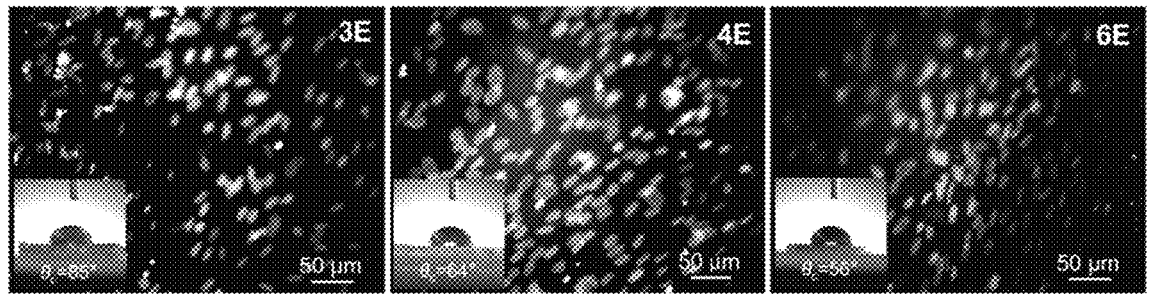
FIG. 10 shows Directionality analysis of primary human dermal fibroblast (hDF) cells grown on: a) 3E, b) 4E, and c) 6E unmodified elastomers.
Figure 11:
FIG. 11 shows Directionality analysis of primary human dermal fibroblast (hDF) cells grown on a) 3LCE-α, b) 4LCE-α, and c) 6LCE-α elastomer films. The insets in each of the images show a photoimage and value from contact angle measurements; The insets in each of the images show a photoimage and value from contact angle measurements.

The fluorescence confocal images and the directional growth analysis histograms of the hDF nuclei are shown and summarized in FIGS. 9-12. The directional analysis histograms of the hDF nuclei growing on commercially available petri dishes are summarized in FIG. 8. FIG. 8 suggests that elongated hDFs are aligned naturally in dense conditions such as almost 100% confluency. All petri dishes showed similar confluence. The dispersion ranges in petri dishes were between 7° and 24°. As seen in FIG. 9 cells on petri dishes, however, show multi maxima in the directionality histograms (multimodal directional distribution), but overall the histograms suggest that cells could potentially grow with a common orientation in some locations of a petri dish.

Figure 12:
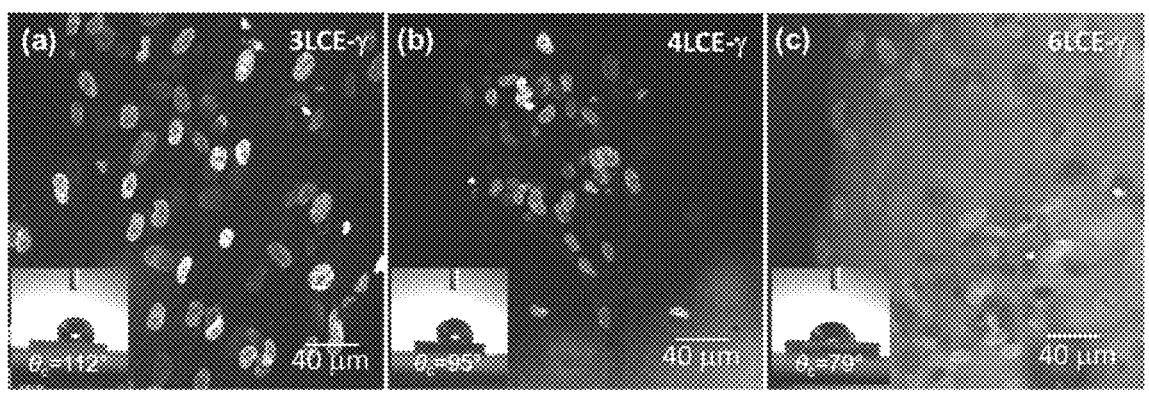
FIG. 12 shows Directionality analysis of primary human dermal fibroblast (hDF) cells grown on a) 3LCE-γ, b) 4LCE-γ, and c) 6LCE-γ elastomer films. The insets in each of the images show a photoimage and value from contact angle measurements.

The hDF cells grew randomly on 3E and 4E. On the other hand, the histogram of 6E shows a somewhat narrower distribution. It suggests that 6E can potentially allow cells to orient within a few locations on the elastomer. Overall, however, there little difference between cells growing on petri dishes and the unmodified elastomers. Analyzing the cells growth on 3LCE-α (FIG. 11*a*) also shows that cell orientation is virtually random, similar to the histograms obtained from analyzing images for cell attachment on petri dishes and the unmodified elastomers. In contrast, and highly noteworthy, the histograms of 4LCE-α and 6LCE-α show that cell attachment and growth are highly anisotropic, with 4LCE-α permitting the highest unimodal cell orientation of hDFs (FIG. 10*b*,*c*). hDF cells on the 3LCE-γ, 4LCE-γ, and 6LCE-γ also show a narrow orientational dispersion of cells (FIG. 12). In comparison, cell orientation on the γ-series LCEs was less uniform in comparison to the α-series LCEs. It was assumed hydrophobicity due to the more flexible LC pendants may contribute to a higher number of cholesterol pendants exposed on the surface of the synthesized γ-series LCEs. Particularly, 4LCE-γ and 6LCE-γ show higher contact angle values than the corresponding 4LCE-α and 6LCE-α, which could potentially inhibit cell growth at the same rate as on the α-series LCEs. Eventually, cells will continue to grow and proliferate but at a lower pace. Cells seeded on elastomers are then incubated following standard tissue culture techniques at about 37° C. with 5% $CO_2$ (or specified for particular cell lines growing protocol), cell media is changed every two-three days (as pertinent for every cell line). Cells are allowed to proliferate for several weeks as predetermined by experimental protocols. We have grown several standard cells used for cell studies, such as SH-SY5Y (neuroblastomas), C2C12 skeletal myoblasts (muscle cells) and primary cell lines (human dermal fibroblasts, hDF). Other examples of cells that can be grown but are not limited to are: stem cells, brain (glial, neurons, etc.), red blood types (erythrocyte), liver (hepatocyte), bone (osteocytes), skin (keratinocyte), endothelial, and muscle (myocite) cells. Our LCEs can be molded, cast, spin coated, electro spun, & 3D printed providing a wide range of shape for multiple uses. LCE can for example molded as a thin bandage and filled with a skin (or stem cells) cells to promote skin regeneration. Other uses can be of 3D printing a particular organ to be filled with particular cell lines to promote organ regeneration.

In summary, the liquid crystal elastomeric scaffolds of the present invention can be used as a drug delivery patch such as for skin, or for internal tissues, tumors, medical implants, and the like, or in the treatment of neurological skin, tissue, organ, etc., or to repair diseased or damaged bones and so forth.

The synthesis, characterization, mechanical, as well as, cell viability studies on smectic-A biocompatible, biodegradable, and porous cholesterol based LCEs have been set forth. In particular, 3-, 4-, and 6-arm (using glycerol, pentaerythritol, or dipentaerythritol) central nodes were investigated as initiators for obtaining star block-copolymers with cholesterol LC molecules as pendant groups within the polymer network. These polymers were further cross-linked to obtain elastomers with cholesterol LC pendants in α- or γ-position to the ε-CL carbonyl group. The type of central node and the position of cholesterol pendants in the backbone of the random ε-CL blocks both affect the overall morphology, the mechanical properties as well as cell proliferation and particularly cell alignment. Mechanical tests showed the highest stiffness for 4LCE-γ, but otherwise no notable difference between the 3- and 6-arm LCEs.

The primary and immortal cells used to evaluate the present invention and grown in a manner as set forth hereinabove have been found to mimic natural cell environment that exist in the real world. Moreover, they have been found to behave physically, mechanically, and biologically functioned as cells grown in their natural environment.

With respect to end use, when applied to a human, creation of dynamic bioscaffolds designed to mimic endogenous structures by the development of biocompatible scaffolds that hold promise for the advancement of tissue engineering to replace or repair diseased or damaged tissues. The LCE materials offer better mechanisms (materials) to reintroduce cells into human bodies and ensure successful reversal of degenerative conditions that human populations face.

While in accordance with the patent statutes, the best mode and preferred embodiment have been set forth, the scope of the invention is not limited thereto, but rather by the scope of the attached claims.

What is claimed:

1. An elastomeric foam scaffold for cells, comprising:
   a one or more elastomeric star block copolymers having at least one arm containing one or more pendant cholesteric or a fluorinated cholesteric liquid crystal thereon that is capable of forming a cholesteric, nematic or a smectic liquid crystal;
   wherein said one or more elastomeric star block copolymers are crosslinked by a polyisocyanate; and
   wherein said elastomeric liquid crystal foam scaffold has a predetermined internal pore morphology derived from a solvent soluble salt or a solvent soluble sugar.

2. The elastomeric foam scaffold of claim 1, wherein a majority of said pores in said scaffold have a predetermined average pore diameter of that of a designated cell including an additional average pore diameter of from about 10% to about 30% greater than said designated cell diameter.

3. The elastomeric foam scaffold of claim 2, wherein said one or more elastomeric star block copolymers have from about 3 to about 8 arms, wherein said star block copolymer is derived from a polyol having from about 3 to about 8 alcohol groups, one or more lactones containing from about 2 to about 6 carbon atoms, one or more halogenated lactones having from about 2 to about 6 carbon atoms, and one or more lactides; wherein said polyisocyanate has from 2 to about 5 isocyanate groups; and wherein said solvent soluble salt comprises an alkali metal salt, and ammonium salt, a halide salt, a carbonate salt, or a sulfate salt, or any combination thereof.

4. The elastomeric foam scaffold of claim 3, wherein said predetermined average pore diameter is the diameter of said designated cell including an additional average pore diameter of from about 15% to about 25% greater than said designated cell diameter.

5. The elastomeric foam scaffold of claim 4, wherein said solvent soluble sugar comprises glucose, fructose, sucrose, or any combination thereof; wherein said polyisocyanate crosslinking agent is hexamethylene diisocyanate, toluene diisocyanate, methyl diphenyl diisocyanate, isophorone diisocyanate, or any combination thereof, or wherein said polyisocyanate comprises a blocked aromatic and/or aliphatic polyisocyanate of said hexamethylene diisocyanate, toluene diisocyanate, methyl diphenyl diisocyanate, or isophorone diisocyanate; and wherein said elastomeric foam scaffold has a porosity of from about 65% to about 95% based upon the total volume of said liquid crystal elastomeric scaffold.

6. The elastomeric foam scaffold of claim 5, wherein said solvent soluble salt comprises sodium chloride or any alkali metal salt, and ammonium salt, a halide salt, a carbonate salt, or a sulfate salt, or any combination thereof; wherein said polyisocyanate comprises hexamethylene diisocyanates; wherein said solvent soluble sugar comprises glucose; and wherein the amount of said pores in said scaffold that have a predetermined average pore diameter is from about 50% to about 95% based upon the total number of pores in said scaffold.

7. The elastomeric foam scaffold of claim 1, including one or more different cultured cells therein, wherein said cells comprise an animal cell or a human cell.

8. The elastomeric foam scaffold of claim 2, including one or more different cultured cells therein, wherein said cultured cells comprise a brain cell, a red blood cell, a hepatocyte cell, an osteogenic cell, an adult mammalian skin cell, a smooth muscle cell, an endothelial cell, or a human skin fibroblast, or any combination thereof.

9. The elastomeric foam scaffold of claim 4, including one or more different cultured cells therein, wherein said cultured cells comprise a brain cell having a cell size of from about 30 to about 70 microns, a red blood cell having a cell size of from about 1 to about 5 microns, a hepatocyte cell having a cell size of from about 20 microns, an osteogenic cell having a cell size of from about 100 to about 300 microns, an adult mammalian skin cell having a cell size of from about 20 to about 125 microns, a smooth muscle cell having a cell size of from about 60 to about 150 microns, an endothelial cell having a cell size of less than about 80 microns, or a human skin fibroblast having a cell size of less than about 160 microns, or any combination thereof.

10. The elastomeric foam scaffold of claim 6, including one or more different synthetic cells therein, wherein said cultured cells comprise a brain cell having a cell size of from about 30 to about 70 microns, a red blood cell having a cell size of from about 1 to about 5 microns, a hepatocyte cell having a cell size of from about 20 microns, an osteogenic cell having a cell size of from about 100 to about 300 microns, an adult mammalian skin cell having a cell size of from about 20 to about 125 microns, a smooth muscle cell having a cell size of from about 60 to about 150 microns, an endothelial cell having a cell size of less than about 80 microns, or a human skin fibroblast having a cell size of less than about 160 microns, or any combination thereof.

11. The elastomeric foam scaffold of claim 3, comprising a specific type of cultured cell in said pores, said cultured cell having an average cell diameter that has a substantially same diameter as an identical naturally existing cell.

12. The elastomeric foam scaffold of claim 9, comprising a specific type of cultured cell in said pores, said cultured cell having an average cell diameter that has a substantially same diameter as an identical naturally existing cell.

13. The elastomeric foam scaffold of claim 7, wherein said elastomer foam scaffold is adaptable for use in a drug delivery patch for skin; or in internal tissues, tumors, medical implants; and in the treatment of neurological skin, tissue, organ, or bone disorders; or any combination thereof.

14. The elastomeric foam scaffold of claim 8, wherein said elastomer foam scaffold is adaptable for use in a drug delivery patch for skin; or in internal tissues, tumors, medical implants; and in the treatment of neurological skin, tissue, organ, or bone disorders;
or any combination thereof.

15. The elastomeric foam scaffold of claim 10, wherein said elastomer foam scaffold is adaptable for use in a drug delivery patch for skin; or in internal tissues, tumors, medical implants; and in the treatment of neurological skin, tissue, organ, or bone disorders; or any combination thereof.

16. A method for forming a polymeric cell scaffold according to claim 1, comprising the steps of:
polymerizing one or more polyols having from about 3 to about 8 alcohol groups, one or more lactones containing from about 2 to about 6 carbon atoms, one or more halogenated lactones having from 2 to about 6 carbon atoms, and one or more lactides and forming a star block copolymer having from 3 to about 8 arms, reacting said star block copolymer with a liquid crystal moiety and forming a liquid crystal containing star block copolymer;
mixing said liquid crystal star block copolymer with a soluble salt, or a soluble sugar, or both, and with at least one polyisocyanate crosslinking agent; and curing said components and forming a polymeric foam scaffold.

17. The method of claim 16, including adding a solvent to said polymeric foam scaffold and leaching said soluble salt or said soluble sugar, or both, from said scaffold and forming an open pore scaffold; wherein the pores in said scaffold have a predetermined pore diameter of a designated cell plus an additional average pore diameter of from about 10% to about 30% greater than said designated cell diameter.

18. The method of claim 17, wherein said soluble salt comprises an alkali metal salt, an ammonium salt, a halide salt, a carbonate salt, or a sulfate salt, or any combination thereof; wherein said soluble sugar comprises glucose, fructose, sucrose, or any combination thereof; and wherein said polyisocyanate crosslinking agent comprises hexamethylene diisocyanate, toluene diisocyanate, methyl diphenyl diisocyanate, isophorone diisocyanate, or any combination thereof.

19. The method of claim 17, including forming a cultured cell in said pores, wherein said cell comprises an animal cell or a human cell.

20. The method of claim 19, wherein said cultured cells comprise a brain cell having a cell size of from about 30 to about 70 microns, a red blood cell having a cell size of from about 1 to about 5 microns, a hepatocyte cell having a cell size of from about 20 microns, an osteogenic cell having a cell size of from about 100 to about 300 microns, an adult mammalian skin cell having a cell size of from about 20 to about 125 microns, a smooth muscle cell having a cell size of from about 60 to about 150 microns, an endothelial cell having a cell size of less than about 80 microns, or a human skin fibroblast having a cell size of less than about 160, or any combination thereof.

* * * * *